(12) United States Patent
Dastillung et al.

(10) Patent No.: US 10,358,396 B2
(45) Date of Patent: Jul. 23, 2019

(54) METHOD FOR THE PRODUCTION OF BUTADIENE AND HYDROGEN FROM ETHANOL IN TWO LOW-WATER AND LOW-ENERGY-CONSUMPTION REACTION STEPS

(71) Applicants: IFP Energies nouvelles, Rueil-Malmaison (FR); Compagnie Generale des Etablissements Michelin, Clermont-Ferrand (FR); MICHELIN RECHERCHE ET TECHNIQUE S.A., Granges-Paccot (CH)

(72) Inventors: Rejane Dastillung, Lyons (FR); Beatrice Fischer, Lyons (FR); Marc Jacquin, Lyons (FR); Raphael Huyghe, Saint Andeol le Chateau (FR)

(73) Assignees: IFP Energies nouvelles, Rueil-Malmaison (FR); Compagnie Generale des Etablissements Michelin, Clermont-Ferrand (FR); MICHELIN RECHERCHE ET TECHNIQUE S.A., Granges-Paccot (CH)

( * ) Notice: Subject to any disclaimer, the term of this patent is extended or adjusted under 35 U.S.C. 154(b) by 0 days.

(21) Appl. No.: 15/511,924

(22) PCT Filed: Sep. 17, 2015

(86) PCT No.: PCT/EP2015/071361
§ 371 (c)(1),
(2) Date: Mar. 16, 2017

(87) PCT Pub. No.: WO2016/042095
PCT Pub. Date: Mar. 24, 2016

(65) Prior Publication Data
US 2017/0291859 A1 Oct. 12, 2017

(30) Foreign Application Priority Data

Sep. 19, 2014 (FR) .................................... 14 58859

(51) Int. Cl.
*C07C 1/207* (2006.01)
*C07C 1/20* (2006.01)
(Continued)

(52) U.S. Cl.
CPC .............. *C07C 1/2076* (2013.01); *C07C 1/20* (2013.01); *C07C 7/005* (2013.01); *C07C 7/11* (2013.01);
(Continued)

(58) Field of Classification Search
CPC .............. C07C 1/207; C07C 1/22; C07C 1/24
See application file for complete search history.

(56) References Cited

U.S. PATENT DOCUMENTS 2,393,381 A * 1/1946 Kinsey .................. C07C 1/2072
585/607
2,395,057 A * 2/1946 Marsh .................. C07C 1/2072
203/39
(Continued)

OTHER PUBLICATIONS

International Search Report for PCT/EP2015/071361 dated Dec. 9, 2015.

*Primary Examiner* — Youngsul Jeong
(74) *Attorney, Agent, or Firm* — Millen, White, Zelano and Branigan, P.C.

(57) ABSTRACT

A process for the production of butadiene from an ethanol feed having at least 80% by weight of ethanol, A) converting ethanol into acetaldehyde B) converting an ethanol/acetaldehyde mixture into butadiene, C1) hydrogen treatment, D1) butadiene extraction, a first butadiene purification D2), a
(Continued)

subsequent butadiene purification D3), an effluent treatment E1), E2) eliminating impurities and brown oils and F) scrubbing with water.

15 Claims, 4 Drawing Sheets

(51) Int. Cl.
 *C07C 7/11* (2006.01)
 *C07C 7/00* (2006.01)
 *C07C 45/00* (2006.01)
(52) U.S. Cl.
 CPC ........ *C07C 45/002* (2013.01); *C07C 2523/20* (2013.01)

(56) References Cited

U.S. PATENT DOCUMENTS

| | | | |
|---|---|---|---|
| 2,403,741 A * | 7/1946 | Murray | C07C 1/2072 585/327 |
| 2,403,742 A * | 7/1946 | Murray | C07C 1/2072 585/327 |
| 2,403,743 A * | 7/1946 | Hitcheock | C07C 1/2072 203/73 |
| 2,409,250 A * | 10/1946 | Cannon | C07C 7/11 585/838 |

\* cited by examiner

METHOD FOR THE PRODUCTION OF BUTADIENE AND HYDROGEN FROM ETHANOL IN TWO LOW-WATER AND LOW-ENERGY-CONSUMPTION REACTION STEPS

FIELD OF THE INVENTION

The invention relates to a process for the production of butadiene from ethanol operating in two reaction steps: a first reaction step producing acetaldehyde, and a second step producing butadiene from a mixture of ethanol and acetaldehyde.

PRIOR ART

Processes for the production of butadiene from ethanol were developed in particular by the Russians, based on work by Lebedev in the 1920s (process with 1 reaction step), and by the Americans during the second world war from the work by Ostromilenski (process with 2 reaction steps—dehydrogenation of ethanol to form acetaldehyde, then production of butadiene from an ethanol/acetaldehyde mixture). This latter process, which can produce slightly better yields, was operated in the United States during the 1940s. All units of this type were stopped long ago, principally for economic reasons.

The process, in its Lebedev or Ostromilenski version, has a conversion per pass substantially below 50%, which implies a lot of recycling, and it is difficult to precisely adjust the ethanol/acetaldehyde ratio at the inlet to the second reactor.

Another problem with the process is the production of a large variety of all sorts of impurities: saturated, unsaturated and aromatic hydrocarbons, but also oxygen-containing products (such as alcohols, phenols, aldehydes, ketones, acids, esters, ethers or acetals).

Certain of these by-products, both gaseous and liquid under normal temperature and pressure conditions, are generated in significant quantities. Gaseous by-products that may be cited include hydrogen, carbon monoxide, carbon dioxide, $C_1$-$C_4$ alkanes and olefins, and methyl ethyl ether. Liquid by-products that may be cited include pentenes, pentadienes, diethyl ether, ethyl vinyl ether, hexenes, hexadienes, butanal, crotonaldehyde, ethyl acetate, diethyl acetal, butanol, hexanol and acetic acid. These gaseous and liquid by-products are problematic as regards obtaining butadiene complying with specifications, but also because recycling them to the reaction steps with ethanol and acetaldehyde induces a reduction in the overall yield from the unit. Extracting them substantially complicates the separation process.

Other by-products are generated in tiny amounts. In the remainder of the document, the term "brown oils" will be used to designate the set of thousands of hydrocarbon and oxygen-containing compounds produced in the reaction sections with boiling points which are between that of ethanol and up to 600° C. These brown oils have the particular feature of being soluble in ethanol but insoluble in water. Particularly when they are not diluted by a large excess of ethanol, they can clog together and block up the equipment. Furthermore, these brown oils are problematic in the distillation column which separates the water produced by the reaction and unconverted ethanol. In fact, these brown oils are soluble in the water-ethanol effluent supplying said distillation column, and insoluble in the residue essentially constituted by water. A phase separation thus occurs in this column, considerably reducing the efficiency of the separation. The brown oils are difficult to eliminate within the process because they are constituted by thousands of compounds having very different physico-chemical properties. A fraction of these brown oils thus accumulates within the process, engendering a drop in its operational efficiency after a few days or weeks at best, and necessitating a periodic purge of certain streams. The resulting loss of ethanol and acetaldehyde degrades the overall yield of the process at a cost which would be prohibitive today.

Because of the numerous impurities produced by the process, the purification of butadiene is complex. It calls upon a combination of numerous unitary operations such as scrubs, simple and extractive distillations. The prior art recommends the use of extractive distillations using a solvent, bis(2-chloroethyl)ether (Chlorex), which is now banned because of its high toxicity. It is important to note that the specifications for butadiene are now extremely severe because of the sensitivity of butadiene polymerization catalysts. Reproducing the prior art concatenation of unitary operations would thus mean that current specifications would not be met. As an example, the specifications for acetaldehyde in butadiene have changed from 1000 ppm to less than 10 ppm today.

The work "Synthetic Rubber", chapter 4 (W. J. Toussaint and J. Lee Marah) provides a general view of the process developed by Carbide and Carbon; the principal steps are summarized below.

The ethanol obtained from an effluent treatment step is converted into an ethanol/acetaldehyde effluent in a first reaction step. This step also produces a gaseous hydrogen effluent. The ethanol/acetaldehyde effluent is then treated in an effluent treatment step, and might have previously been sent to a butadiene extraction step so as to separate an ethanol effluent and an acetaldehyde effluent. The ethanol/acetaldehyde effluent contains a large quantity of acetaldehyde (approximately 20% by weight), which is much more volatile than ethanol, and thus is more easily entrained in the gaseous effluent.

The hydrogen effluent is treated in a water scrubbing step which can be used to recover the ethanol and acetaldehyde entrained with the hydrogen. An efficient scrub, meaning that the overall yield of the unit is not reduced by a loss of ethanol and acetaldehyde, involves using at least 2 tonnes of water per tonne of butadiene produced or an equivalent of the order of 5 tonnes of water per tonne of acetaldehyde and ethanol recovered. The scrubbing water must then be treated in an effluent treatment step. The recovery of traces of ethanol and acetaldehyde thus provides a substantial increase in the size of the equipment and the energy consumption of the process. The purity of the hydrogen is of the order of 99 molar % or 90% by weight.

The second reaction step for conversion of an ethanol/acetaldehyde mixture into butadiene is supplied by the ethanol and the acetaldehyde obtained from an effluent treatment step. It produces a liquid effluent and a gaseous effluent. The fact of separating the products obtained from the first reaction step in a step for the treatment of effluents to mix them afresh at the inlet to the second reaction step entrains an increase in the size of the equipment and the energy consumption of the process.

In the prior art, the gaseous effluent obtained from the second reaction step is scrubbed with effluents that are rich in ethanol but impure, which has the result of requiring the butadiene extraction step and the step for the treatment of the gaseous by-products to be over-dimensioned, and thus the treatment step for the effluents as well.

The effluents from the second reaction step are treated in a butadiene extraction step, which is also supplied with a portion of the ethanol/acetaldehyde effluent obtained from the first reaction step. This step comprises at least one gas-liquid scrubbing section and a distillation section. This extraction step produces a crude butadiene effluent, a gaseous products effluent, and an ethanol/acetaldehyde/water effluent. This latter may be recycled to the head of the gas-liquid scrubbing section of the step. However, this recycle is problematic, as the presence of water in the ethanol reduces the solubility of butadiene. Thus, the liquid flow rates have to be increased in order to extract the same quantity of butadiene from the scrubbed gaseous stream in order to compensate for the reduction in solubility.

The unrefined butadiene is scrubbed with water in a first purification step, then purified in a subsequent purification step, inter alia by extractive distillation employing a solvent of the bis(2-chloroethyl)ether (Chlorex) type. The water obtained from scrubbing the unrefined butadiene is treated in an effluent treatment step and the impurities obtained from the subsequent purification are eliminated from the process.

The first butadiene purification step can be used to eliminate the acetaldehyde present in the unrefined butadiene obtained from the butadiene extraction step. However, because of the change in the carbonyl specifications in the butadiene between the 1960s and today, the flow rate of water supplying the first butadiene purification step has to be increased very substantially in order to obtain the current specifications. The spent water effluent generated thereby is sent to the effluent treatment step, and so complying with the specifications translates into a substantial increase in the size of the equipment and in the energy consumption. In addition, the increase in the flow rate of the scrubbing water in order to comply with the specifications also translates into problems with butadiene/water demixing in the scrubbing column.

The effluent treatment step means that, starting from the various treated effluents, an acetaldehyde effluent, an ethanol effluent, a water effluent, a liquid by-product effluent and optionally a brown oil effluent can be separated. This step generally comprises two or three distillation columns. The ethanol feed for the process is supplied to the effluent treatment step at the ethanol/water distillation level.

The brown oil effluent which is possibly produced in this step is either eliminated from the process or treated in a specific step for the treatment of the liquid by-products and brown oils in order to produce various upgradable effluents, such as an effluent which is rich in ethyl acetate or indeed an effluent which is rich in hexadienes and aimed at minimizing the losses of ethanol and acetaldehyde with the liquid by-products and the brown oils.

The complexity of the recycles between the various unitary operations of the effluent treatment step renders this step difficult to operate. Furthermore, the phase separations which occur in the columns, in particular due to the brown oils, are problematic as regards operation, but also as regards the dimensions of the equipment.

The gaseous by-products are treated in a step for the treatment of gaseous by-products in which they are scrubbed with a stream of water which latter is then treated in the effluent treatment step.

U.S. Pat. No. 1,977,750 describes the steps of conversion of ethanol into acetaldehyde and treatment of hydrogen. The ethanol is partially converted in a catalytic section. The effluent, which is principally constituted by ethanol, acetaldehyde and hydrogen, is cooled in a water condenser, then in a condenser supplied with brine, before being scrubbed with water. The set of liquid effluents collected in these three unitary operations are combined and distilled in order to recover the unconverted acetaldehyde and ethanol.

U.S. Pat. No. 2,249,847 describes the steps for conversion of ethanol into acetaldehyde, and of treatment of effluents in the case of a process which produces only acetaldehyde and its by-products. In particular, it describes the importance of introducing the ethanol feed into the reflux drum of the ethanol/water distillation column of the effluent treatment step, which practice is reproduced in all subsequent documents.

U.S. Pat. No. 2,403,741 describes the steps for conversion of ethanol to acetaldehyde, conversion of an ethanol/acetaldehyde mixture into butadiene, the treatment of hydrogen, extraction of butadiene, first purification of butadiene, and treatment of the effluents. It describes the importance of using the ethanol/acetaldehyde effluent obtained from the first reaction step to carry out the step for extraction of butadiene comprised in the vapour effluent obtained from the second reaction step.

U.S. Pat. No. 2,403,742 describes the steps for conversion of ethanol to acetaldehyde, conversion of an ethanol/acetaldehyde mixture into butadiene, the treatment of hydrogen, extraction of butadiene, first purification of butadiene, and treatment of the effluents. It describes the difficulty of recycling an acetaldehyde effluent obtained from the step for treatment of the effluents towards the second reaction step, in particular because of the presence of diethyl ether which forms an azeotrope with the acetaldehyde. The step for treatment of the effluents thus uses an intermediate distillation column between that producing the acetaldehyde and that producing the ethanol in order to eliminate the liquid by-products. This practice is also seen in all subsequent documents.

U.S. Pat. Nos. 2,403,743, 2,393,381 and 2,395,057 describe various configurations of the step for treatment of the effluents and the optional presence of a step for the treatment of the liquid by-products and brown oils in order to minimize the losses of ethanol and acetaldehyde. These documents show us that without carrying out the inventions described, the purity of the acetaldehyde effluent obtained from the step for the treatment of the effluents would drop below 50% by weight, engendering severe problems when this effluent is recycled to the second reaction step. The inventions proposed can be used to obtain an acetaldehyde/ethanol effluent obtained from the effluent treatment step with a purity of more than 80% by weight, and in the best case equal to 93% by weight. However, the separation trains described are clearly difficult to operate and devour energy because of the many recycles between the various unitary operations.

U.S. Pat. No. 2,409,250 (Carbide and Carbon, 1944) describes the successive butadiene purification steps (extraction, first purification and subsequent purification of butadiene by super-fractionation). The butadiene is produced in a purity of 98.7%, but at the cost of a significant loss of yield. In order to limit this loss, the overhead products from the columns for the purification of butadiene by super-fractionation are withdrawn and recycled in part to the butadiene extraction step. These substantial recycles, in particular recycling the butane/butadiene stream with a view to eliminating incondensable, involve over-dimensioning the equipment.

In U.S. Pat. No. 2,439,587, Koppers proposes an improvement to the Carbide and Carbon process, consisting of recovering the ethyl acetate by-product and recycling it to the second reaction step. The separation operations are complex and difficult to regulate as they employ, inter alia, side streams, decantations, purges and scrubbing with water, and induce large losses of ethanol and acetaldehyde.

U.S. Pat. No. 1,948,777 (Carbide and Carbon, 1931) describe in detail the subsequent step for purification of butadiene by extractive distillation using various solvents, including Chlorex. By limiting the loss of butadiene at the column head, i.e. a concentration of 0.2% of butadiene in the distillate, the purity of the butadiene obtained at the bottom is only 70%, while in seeking to obtain a more pure butadiene at the bottom, i.e. 99%, the overhead butadiene loss is much higher, with a concentration of butadiene in the distillate of 30%. Thus, high purity butadiene is produced at the price of a drop in the overall yield from the unit.

The overall yield of prior art layouts is low given that the acetaldehyde effluent recycled to the second reaction step is impure and because of the losses of ethanol and acetaldehyde.

Even though the current principal source of butadiene is from oil, the future loss of fields has led to a complete rethink of the old process in order to allow butadiene to be produced from an alternative source.

Aim and Advantage of the Invention

The invention provides a process for the production of butadiene from an ethanol feed comprising at least 80% by weight of ethanol, comprising at least:

A) a step for conversion of the ethanol to acetaldehyde, comprising at least one reaction section supplied with at least a fraction of ethanol-rich effluent obtained from step E1), operated at a pressure in the range 0.1 to 1.0 MPa and at a temperature in the range 200° C. to 500° C. in the presence of a catalyst, and a separation section for separating the effluent from said reaction section into at least one hydrogen effluent in the gaseous form and an ethanol/acetaldehyde effluent in the liquid form;

B) a step for conversion into butadiene, comprising at least one reaction section supplied with at least a fraction of said ethanol/acetaldehyde effluent obtained from step A), with an ethanol-rich liquid obtained from step C1), with a fraction of the acetaldehyde-rich effluent obtained from step E1), operated in the presence of a catalyst, at a temperature in the range 300° C. to 400° C., and at a pressure in the range 0.1 to 1.0 MPa, the supply flow rates being regulated such that the ethanol/acetaldehyde molar ratio at the inlet to said reaction section is in the range 1 to 5, and a separation section for separating the effluent from said reaction section into at least one gaseous effluent and a liquid effluent;

C1) a hydrogen treatment step, comprising at least one compression section compressing said hydrogen effluent obtained from step A) to a pressure in the range 0.1 to 1.0 MPa, and a gas-liquid scrubbing section supplied, at a temperature in the range 15° C. to −30° C., with a fraction of said ethanol effluent obtained from step E1) and with a fraction of said ethanol/acetaldehyde effluent obtained from step A), and supplied, at a temperature in the range 25° C. to 60° C., with said compressed hydrogen effluent, and producing at least one liquid ethanol-rich effluent and a purified hydrogen effluent;

D1) a step for extraction of butadiene, comprising at least one compression section compressing said gaseous effluent obtained from step B) to a pressure in the range 0.1 to 1.0 MPa, a gas-liquid scrubbing section comprising a scrubbing column supplied overhead, at a temperature in the range 20° C. to −20° C., with an ethanol stream constituted by said ethanol feed for the process and/or a fraction of the ethanol effluent obtained from step E1) and at the bottom with said gaseous effluent obtained from step B) and cooled, and a distillation section operated at a pressure in the range 0.1 to 1 MPa, supplied with at least the liquid effluent obtained from said step B) and with the liquid effluent from said gas-liquid scrubbing section, said step D1) producing at least one effluent of gaseous by-products, an unrefined butadiene effluent and an ethanol/acetaldehyde/water effluent;

D2) a first butadiene purification step comprising at least one gas-liquid scrubbing section the bottom of which is supplied with the unrefined butadiene effluent obtained from D1) and the head of which is supplied with a stream of water which may be a stream of water with an origin external to said butadiene production process and/or a fraction of the water effluent obtained from step E1), said scrubbing section producing a pre-purified butadiene effluent overhead and a spent water effluent from the bottom;

D3) a subsequent butadiene purification step supplied with at least said pre-purified butadiene effluent obtained from said step D2), and producing at least one purified butadiene effluent;

E1) an effluent treatment step supplied with at least the water/ethanol/acetaldehyde raffinate obtained from step E2), and producing at least one ethanol-rich effluent, an acetaldehyde-rich effluent and a water-rich effluent;

E2) a step for eliminating impurities and brown oils, supplied with at least the ethanol/acetaldehyde/water effluent obtained from step D1), and with the water-rich effluent obtained from step E1), and producing at least one water/ethanol/acetaldehyde raffinate, a light brown oil effluent and a heavy brown oil effluent;

F) a step for scrubbing with water supplied by the effluent of gaseous by-products obtained from step D1), as well as with a fraction of the water-rich effluent obtained from said step E1) and producing at least one alcohol-containing water effluent.

The Applicant has identified an arrangement of unitary operations which can be used to overcome the numerous disadvantages of the prior art. In particular, the arrangement of unitary operations of the invention can be used to eliminate gaseous impurities, liquid impurities and brown oils while minimizing the loss of ethanol and acetaldehyde, thereby improving the overall yield of the unit while reducing the overall flow of water necessary for the separation steps and obtaining a very pure butadiene. The large reduction in the overall flow of water means that the energy consumption of the process can be reduced, along with the dimensions of the separation equipment.

DETAILED DESCRIPTION OF THE INVENTION

Feed

The ethanol feed used in the process of the invention may be of any origin—fossil, plant or animal—, and in particular from processes for the production of ethanol from plant resources. Said feed comprises at least 80% by weight of ethanol, preferably at least 90% by weight, and preferably at least 93% by weight. Highly preferably, said ethanol feed satisfies EN 15376 ethanol fuel specifications.

Step A) for the Conversion of Ethanol into Acetaldehyde

In accordance with the invention, a step A) for the conversion of ethanol into acetaldehyde comprises at least one reaction section supplied with at least a fraction of ethanol-rich effluent obtained from step E1), said fraction preferably constituting at least 10% of the flow rate of said ethanol-rich effluent obtained from step E1), and optionally advantageously supplied with at least a fraction of said ethanol feed, and a separation section for separating the effluent from said reaction section into at least one hydrogen effluent in the gaseous form and an ethanol/acetaldehyde effluent in the liquid form.

Said reaction section can be used to convert ethanol into acetaldehyde in the presence of a catalyst preferably consisting of a mixture of chromium oxide and copper oxide, or any other suitable catalyst. These catalysts are well known to the skilled person.

Said reaction section is operated at a pressure in the range 0.1 to 1.0 MPa, preferably in the range 0.1 to 0.5 MPa, preferably in the range 0.1 to 0.3 MPa, and at a temperature in the range 200° C. to 500° C., preferably in the range 250° C. to 300° C.

Preferably, the ethanol conversion is in the range 30% to 40%, with a selectivity in the range 85% to 100% towards acetaldehyde, preferably in the range 90% to 95% towards acetaldehyde. The effluent from said reaction section also comprises by-products such as crotonaldehyde, butyraldehyde, diethylacetal, ethyl acetate and acetic acid.

Said separation section uses gas-liquid separation means known to the skilled person. Preferably, a gas-liquid separator operated at a pressure in the range 0.1 to 0.3 MPa and at a temperature in the range 25° C. to 60° C. is used.

Step B) for the Conversion of an Ethanol/Acetaldehyde Mixture into Butadiene

In accordance with the invention, a step B) for conversion into butadiene comprises at least one reaction section supplied with at least a fraction of said ethanol/acetaldehyde effluent obtained from step A), with an ethanol-rich liquid effluent obtained from step C1), with a fraction of the acetaldehyde-rich effluent obtained from step E1) and advantageously and optionally supplied with an ethanol-rich stream obtained from step E1), and a separation section for separating the effluent from said reaction section into at least one gaseous effluent and a liquid effluent. Said reaction section may also be supplied with an external stream of acetaldehyde.

The flow rate of the various supplies to the reaction section of said step B) is adjusted such that the molar ratio of ethanol to acetaldehyde at the inlet to said reaction section is in the range 1 to 5, preferably in the range 1 to 3.5, more preferably in the range 2 to 3 and highly preferably in the range 2.4 to 2.7.

Said reaction section can be used to convert a portion of the ethanol/acetaldehyde mixture into at least butadiene. The selectivity of the transformation of the ethanol/acetaldehyde mixture is preferably more than 60%, more preferably more than 70%, highly preferably more than 80%. The term "selectivity" means the molar ratio of the flow rate of butadiene in the effluent from said reaction section to the flow rate of ethanol and acetaldehyde consumed in said reaction section. The conversion of the transformation of the ethanol/acetaldehyde mixture is preferably more than 30%, more preferably more than 40%, preferably more than 47%. The term "conversion" means the molar ratio of the flow rate of ethanol and acetaldehyde in the effluent from said reaction section with respect to the flow rate of ethanol and acetaldehyde in the supply to said reaction section. It is operated in the presence of a catalyst, advantageously a catalyst supported on silica selected from the group constituted by catalysts comprising tantalum oxide, zirconium or colombium, preferably comprising 2% of tantalum oxide (see, for example, Corson, Jones, Welling, Hincbley, Stahly, Ind. Eng Chem. 1950, 42, 2, 359-373). Said reaction section is operated at a temperature in the range 300° C. to 400° C., preferably in the range 320° C. to 370° C., and at a pressure in the range 0.1 to 1.0 MPa, preferably in the range 0.1 to 0.5 MPa, preferably in the range 0.1 to 0.3 MPa.

Preferably, approximately 65% to 80% of the acetaldehyde is converted in said reaction section. The effluent from said reaction section thus still comprises ethanol. Many impurities may be produced with the butadiene, including ethylene, propylene, diethyl ether (DEE), ethyl acetate, butanol, hexanol, butenes, pentenes, pentadienes, hexenes and hexadienes.

Said reaction section is supplied with the acetaldehyde effluent obtained from step E1) for the treatment of effluents, the ratio of ethanol to acetaldehyde at the inlet to this section being adjusted by controlling the fraction of the ethanol effluent obtained from said step E1) supplying the step A), and thus producing acetaldehyde. In fact, the remaining fraction of the ethanol-rich effluent obtained from said step E1) supplies the step C1) for the treatment of hydrogen and, after scrubbing the hydrogen effluent, forms said ethanol-rich liquid effluent obtained from said step C1) which is supplied to said step B). However, this ethanol-rich liquid effluent obtained from said step C1) contains only very little acetaldehyde. Thus, controlling the ethanol to acetaldehyde ratio at the inlet to said reaction section is easy with the process of the invention.

Said separation section uses gas-liquid separation means which are known to the skilled person. Preferably, a gas-liquid separator is used which is operated at a pressure in the range 0.1 to 0.3 MPa and at a temperature in the range 25° C. to 60° C.

Step C1) for Treatment of Hydrogen

In accordance with the invention, a hydrogen treatment step C1) comprises at least one compression section supplied with said hydrogen effluent obtained from step A), and a gas-liquid scrubbing section supplied with a fraction of said ethanol effluent obtained from step E1) and with a fraction of said ethanol/acetaldehyde effluent obtained from step A), and produces at least one liquid ethanol-rich effluent and a purified hydrogen effluent. Preferably, said step C1) is not supplied with any other stream.

Said fraction of said ethanol/acetaldehyde effluent obtained from step A) is in the range 0 to 100%. Using a fraction of said ethanol/acetaldehyde effluent means that the flow rate of the fraction of said ethanol-rich effluent obtained from said step E1) can be reduced.

Said step C1) can be used to obtain a high purity purified hydrogen effluent, i.e. comprising at least 90 molar % of hydrogen, preferably 99 molar % of hydrogen, preferably 99.8 molar % of hydrogen. The purified hydrogen effluent also comprises traces of water and ethanol. This step can also be used to recover ethanol and acetaldehyde comprised in the hydrogen effluent obtained from said step A), thereby allowing them to be recycled and to maximize the overall yield of the process.

The use of a fraction of ethanol-rich effluent obtained from step E1) and an ethanol/acetaldehyde effluent fraction obtained from step A) instead of water—as was the case in the prior art—means that the total flow rate of water moving in the process can be reduced. Thus, the total flow rate of water supplying steps E1) and E2) for treatment of the effluents is reduced, thereby reducing the size of the equipment and the consumption of utilities in steps E1) and E2). In addition, as described above, the ethanol-rich liquid effluent obtained from said step C1) can be used to supply butadiene conversion step B) directly without having to be treated in effluent treatment step E1).

The Applicant has discovered that, in the process of the invention, ethanol is a much better solvent than water for scrubbing acetaldehyde, which means that the dimensions of the equipment used in step C1) of the invention can be reduced compared with the prior art.

The hydrogen effluent obtained from step A) is compressed in a compression section to a pressure in the range 0.1 to 1.0 MPa, advantageously in the range 0.1 to 0.7 MPa, and preferably in the range 0.4 to 0.68 MPa. The effect of this compression is on the one hand to reduce the volume flow rate of gas, and on the other hand to improve the efficiency of the downstream scrubbing.

The compressed hydrogen effluent is then cooled to a temperature in the range 25° C. to 60° C., preferably in the range 30° C. to 40° C., then supplied to the bottom of the scrubbing column of the scrubbing section in which it is brought into contact with said fraction of the ethanol effluent obtained from step E1) and said fraction of the ethanol/acetaldehyde effluent obtained from step A), said fractions respectively being supplied to the head and to an intermediate point of said scrubbing column. These two fractions are each cooled to a temperature in the range 15° C. to −30° C., preferably in the range 0° C. to −15° C., before being supplied to said scrubbing column. Advantageously, the effluent which is rich in ethanol obtained from step E1) is supplied at a temperature which is lower than that of said fraction of the ethanol/acetaldehyde effluent obtained from step A), thereby creating a thermal gradient between the head and the bottom and limiting the losses of solvent in the purified hydrogen effluent. The gas-liquid scrubbing column of the scrubbing section is provided with plates or loose or structured packing.

The Applicant has discovered that the presence of a large quantity of ethanol compared with water in said scrubbing section means that lower operating temperatures can be employed without running the risk of forming hydrates in this column. The low temperature of the scrubbing liquids and the temperature gradient between the head and bottom means that a very good recovery of acetaldehyde present in the compressed hydrogen effluent can be obtained, along with very high purity of the purified hydrogen effluent withdrawn from the head of said scrubbing section. Thus, the loss of acetaldehyde in the purified hydrogen effluent is zero. In addition, the loss of ethanol in the purified hydrogen is very low because of the low temperature of the ethanol introduced to the head of the scrubbing section, which is authorized by the absence of hydrate formation.

Optional Step C2) for Final Treatment of the Hydrogen Effluent

A final hydrogen treatment step C2) is advantageously carried out at the end of step C1). Said step C2) comprises at least one gas-liquid scrubbing section supplied with the purified hydrogen effluent obtained from C1) and with a pure at water effluent originating from outside the process or with a water-rich effluent obtained from step E1), and produces a purified hydrogen effluent and a spent water effluent.

Said scrubbing section comprises at least one gas-liquid scrubbing column supplied at the bottom with said purified hydrogen effluent obtained from C1), and overhead with a pure water effluent or by a water-rich effluent obtained from step E1) and producing a purified hydrogen effluent overhead and a bottom spent water effluent.

This step can be used to recover the final traces of ethanol that may be contained in the purified hydrogen effluent obtained from C1). Said step C2), similar to the hydrogen treatment of the prior art, nevertheless employs much lower water flow rates than those used in the prior art, the hydrogen effluent supplying step C2) having already been treated in step C1), and thus freed from all of the acetaldehyde entrained in the hydrogen effluent obtained from step A). With everything else being equal, the elimination of traces of ethanol by scrubbing with water demands lower flow rates than the elimination of traces of acetaldehyde. In addition, since ethanol is less volatile than acetaldehyde, under the same operating conditions, it is entrained to a much lesser extent than acetaldehyde.

Butadiene Extraction Step D1)

In accordance with the invention, a step D1) for extraction of butadiene comprising at least one compression section, a gas-liquid scrubbing section and a distillation section is supplied with at least said gaseous and liquid effluents obtained from said step B), with an ethanol stream constituted by said ethanol feed of the process and/or a fraction of the ethanol effluent obtained from step E1), and produces at least one effluent of gaseous by-products, an unrefined butadiene effluent and an ethanol/acetaldehyde/water effluent.

Said ethanol stream supplying step D1) preferably comprises at least 80% by weight of ethanol, preferably at least 90% by weight, and preferably at least 93% by weight. Said ethanol stream supplying step D1) may contain methanol, water, ethyl acetate, butanol and hexanol. Preferably, said ethanol stream supplying step D1) comprises less than 10% by weight of acetaldehyde, preferably less than 5% by weight, and more preferably less than 1% by weight. Preferably, said ethanol stream supplying step D1) comprises less than 20% by weight of water, preferably less than 5% by weight, more preferably less than 1% by weight.

In a preferred arrangement, said ethanol stream supplying step D1) is constituted by said ethanol feed for the process. One advantage of this arrangement is that said feed is free of by-products from the reactions which are formed in steps A) and B) and which may become concentrated by means of the recycles. In particular, this ethanol feed does not contain acetaldehyde, or only in trace amounts.

In another preferred arrangement, said ethanol stream is constituted by a fraction of the ethanol effluent obtained from effluent treatment step E1).

The use of an ethanol stream containing little or no acetaldehyde minimizes the entrainment of acetaldehyde in said effluent of gaseous by-products withdrawn from the head of said gas-liquid scrubbing section, reducing the losses in the overall yield of the process, as well as the necessary flow rate of the scrubbing water in step F).

The gaseous effluent obtained from step B) is compressed in said compression section to a pressure in the range 0.1 to 1.0 MPa, preferably in the range 0.1 to 0.7 MPa, and preferably in the range 0.2 to 0.5 MPa. The effect of this compression is on the one hand to reduce the volume flow rate of gas, and on the other hand to improve the downstream scrubbing efficiency. Preferably, the compressed gaseous effluent is then cooled to a temperature in the range 25° C. to 60° C., preferably in the range 30° C. to 40° C.

Preferably, said gas-liquid scrubbing section of step D1) comprises a scrubbing column with an overhead supply of said ethanol stream supplying step D1), and with a bottom supply of said compressed and cooled gaseous effluent, and produces the gaseous by-products as an overhead effluent and a bottom liquid effluent which is supplied to said distillation section of step D1).

Said ethanol stream supplying step D1) is cooled before being supplied to the head of said gas-liquid scrubbing column of the scrubbing section at a temperature in the range 20° C. to −20° C., preferably in the range 15° C. to 5° C. The importance of cooling said ethanol stream is to improve the performance of the scrubbing operation by minimizing the entrainment of ethanol and acetaldehyde in said effluent of gaseous by-products. Thus, all of the butadiene present in the compressed and cooled gaseous effluent obtained from step B) is scrubbed and the effluent vapour of by-products withdrawn from the head of said gas-liquid scrubbing section is free from butadiene.

Minimizing the acetaldehyde entrainment in said effluent of gaseous by-products can incidentally substantially reduce the flow rate of water required in step F) for scrubbing the gaseous by-products with water, the aim of which is to recover ethanol and any traces of acetaldehyde entrained in the effluent of gaseous by-products withdrawn from the head of the ethanol scrubbing section of step D1).

Preferably, the ethanol stream enriched in butadiene withdrawn from the bottom of said gas-liquid scrubbing section of step D1) as well as the liquid effluent obtained from step B) supply said distillation section of step D1) in order to separate an overhead vapour effluent comprising the majority of the butadiene, termed the unrefined butadiene effluent, and an ethanol/acetaldehyde/water residue from the bottom. The term "majority" means more than 80% of the butadiene comprised in the supply to said distillation section, preferably more than 90%, more preferably more than 95%, still more preferably more than 98%, highly preferably more than 99% and highly advantageously all of the butadiene comprised in said supply. This ethanol/acetaldehyde/water residue comprises ethanol and acetaldehyde and also comprises water produced in step B) and by-products formed in steps A) and B) such as, for example, diethyl ether and ethyl acetate and brown oils. Said ethanol/acetaldehyde/water residue then supplies the effluent treatment step E2). Said distillation section is operated at a pressure in the range 0.1 to 1 MPa, preferably in the range 0.2 to 0.5 MPa.

The arrangement of the recycles and the use of external streams (ethanol feed, water) of the invention, and in particular a cooled ethanol stream, means that the flow rate of the spent water effluent can be minimized, along with the flow rate to be treated by said sections E1) and E2). The process of the invention can thus be used to minimize the flow rate of the effluents to be treated in the effluent treatment step.

First Butadiene Purification Step D2)

The first butadiene purification step D2) comprises at least one gas-liquid scrubbing section the bottom of which is supplied with the unrefined butadiene effluent obtained from D1) and the head of which is supplied with a stream of water which may be a stream of water with an origin external to said butadiene production process and/or a fraction of the water effluent obtained from step E1), said scrubbing section producing a pre-purified butadiene effluent overhead and a spent water effluent from the bottom. Preferably, said water stream is a stream of water which originates outside the process.

Said spent water effluent contains acetaldehyde and a little butadiene and may be sent to the step E1) for the treatment of effluents, towards the acetaldehyde distillation section or towards step E2).

The aim of step D2) is to eliminate polar impurities, in particular acetaldehyde, which must not be present in the final butadiene in amounts beyond a few ppm. The unrefined butadiene effluent obtained from D1) comprises mainly butadiene, but still contains many impurities including a large quantity of acetaldehyde which forms an azeotrope with the butadiene and thus cannot be completely eliminated by distillation during step D1). Thus, the flow rate of said stream of water is adjusted in order to obtain the desired specification for acetaldehyde in the pre-purified butadiene effluent.

Said stream of water is cooled to a temperature below 25° C., preferably below 20° C. before supplying the gas-liquid scrubbing section so as to carry out scrubbing with a reduced quantity of water. The supply temperature for said stream of water is selected so that no hydrates are formed with the butadiene and the light hydrocarbons still present in the unrefined butadiene stream obtained from step D1). The pressure of the scrubbing column is determined so as to ensure that there is no condensation of butadiene and that it remains in the gaseous form. The pressure on this step is in the range 0.1 to 1 MPa, preferably in the range 0.2 to 0.3 MPa.

Optional Second Butadiene Purification Step D2bis)

The pre-purified butadiene effluent obtained from step D2) advantageously undergoes a second butadiene purification step D2bis) before being supplied to the subsequent butadiene purification step D3), said step D2bis) comprising at least one scrubbing section the bottom of which is supplied with said pre-purified butadiene effluent obtained from D2), and the head of which is supplied with an absorbent solution. A pre-purified butadiene effluent is withdrawn from the head of said scrubbing section from which traces of acetaldehyde still contained in the pre-purified butadiene effluent have been eliminated, as well as traces of other carbonyls which are less soluble in water than in acetaldehyde such as, for example, butanal, acetone and hexanal, and thus less effectively eliminated by a simple scrub with water. A liquid effluent is withdrawn from the bottom of said scrubbing section which is eliminated from the process.

In a first embodiment of said step D2bis), said absorbent solution is an aqueous solution with a pH of more than 10, adjusted by adding sodium or potassium hydroxide.

In a second embodiment of said step D2bis), said absorbent solution is an aqueous solution of sodium or potassium bisulphite the pH of which is in the range 5 to 8, preferably in the range 6 to 7.

In a third embodiment of said step D2bis), said absorbent solution is an aqueous solution containing a compound from the hydrazine family.

The Applicant has discovered that the combination of steps D2) and D2bis) is particularly well suited to the treatment of an unrefined butadiene effluent obtained from a process for the production of butadiene from ethanol.

In fact, carrying out step D2) alone necessitates large flow rates of water in order to comply with the specification of less than 10 ppm of carbonyl compounds. These large water flow rates are then treated in step E1), which entails considerable operating and investment costs. In addition, by very greatly increasing the flow rates of water supplying step D2), a small portion of butadiene is dissolved, which reduces the overall yield of the process.

Furthermore, carrying out step D2bis) alone would not be suitable for treating an unrefined butadiene effluent obtained from step D1). In fact, the acetaldehyde eliminated from the unrefined butadiene effluent by contact with a basic aqueous solution or a bisulphite solution or an aqueous solution of a compound from the hydrazine family cannot readily be regenerated. As a consequence, a large quantity of acetaldehyde would then be lost, which would lead to a drop in the overall yield of the process.

Thus, the Applicant has identified an optimized function of the process by concatenating the steps D2) and D2bis) of the first and second butadiene purification, meaning that the specifications can be complied with respectively while maximizing the overall yield of the process and minimizing the operating costs.

Subsequent Butadiene Purification Step D3)

In accordance with the invention, a subsequent butadiene purification step D3) is supplied with at least said pre-purified butadiene effluent obtained from said step D2), advantageously treated in the second purification step D2bis), and produces at least one purified butadiene effluent.

This step D3) can be used to purify the butadiene produced in the reaction steps to a very high degree of purity (more than 99.5% by weight, preferably more than 99.8% by weight and highly preferably more than 99.9% by weight), while limiting the losses of product by separating the impurities which have not or have only partially been removed during step D1), D2) and advantageously D2bis).

In a first embodiment of the invention, said step D3) comprises at least one drying section, a cryogenic distillation section and a butadiene/butenes separation section using liquid-liquid extraction.

The pre-purified butadiene effluent obtained from step D2), advantageously treated in step D2bis), is supplied to a drying section. This section is intended to comply with the required specifications for water in the final product (purified butadiene effluent) and to allow cryogenic separation to be carried out without the risk of hydrate formation. A dry butadiene effluent is obtained at the outlet from said drying section. The term "dry butadiene" means less than 10 ppm of water, preferably less than 5 ppm, more preferably less than 1 ppm.

Said drying section preferably comprises drying constituted by one or more chambers containing one or more adsorbents with a high affinity for water. In non-limiting manner, this adsorbent may be constituted by silica and/or alumina. In non-limiting manner, this adsorbent may be a zeolite such as zeolite 3A or 4A. When the adsorbent or adsorbents are saturated with water, said pre-purified butadiene effluent is supplied to another chamber containing adsorbent or fresh or regenerated adsorbents.

The adsorbent may be regenerated either by modifying the partial pressure of water in the chamber, or by modifying the temperature in the chamber, or by modifying the temperature in the chamber, or by modifying the partial pressure of water and the temperature in the chamber. In this latter embodiment, regeneration of the water-saturated adsorbent or adsorbents is carried out by heating the chamber, while supplying it with a stream containing little or no water. The term "little or no water" means less than 500 ppm, preferably less than 350 ppm, preferably less than 10 ppm, preferably less than 5 ppm, highly preferably less than 1 ppm. In a non-limiting manner, this stream containing little or no water may be a stream of nitrogen, a stream of air, a stream of hydrocarbon, or a stream of hydrogen. In a preferred embodiment of the invention, a fraction of the purified hydrogen effluent obtained from step C1) is used.

Said stream containing little or no water is heated to a temperature sufficient to regenerate the adsorbent or adsorbents before being supplied to the chamber containing the adsorbent or adsorbents to be regenerated, preferably to approximately 250° C.

In this first embodiment, said dry butadiene effluent is then supplied to a cryogenic distillation section employing a distillation column. The light products leave the head of the cryogenic distillation section between −25° C. and −35° C. The column bottom is at a temperature in the range 20° C. to 50° C., preferably between 25° C. and 45° C., highly preferably between 30° C. and 40° C.; the overhead column pressure is in the range 0.3 to 0.4 MPa, preferably 0.35 MPa. The advantage of the column is that it can provide very good separation efficiency for the latter incondensables, without a loss of butadiene (less than 0.05%). Thus, a substantial recycle to step D1) and a loss of butadiene are avoided.

Still in this first embodiment, the bottom product from said cryogenic distillation section, termed the topped butadiene effluent, comprises butenes as the principal impurity. Said topped butadiene effluent supplies a liquid-liquid butadiene/butenes extraction section such as that described in patent FR 2 036 057.

Said butadiene/butenes separation section is a liquid-liquid extraction section in which said topped butadiene effluent is supplied, at an intermediate zone, to a first liquid-liquid extraction column into which a stream of polar solvent, preferably DMSO, is supplied to the head. The bottom is supplied with a saturated hydrocarbon solvent, preferably pentane or cyclohexane. The flow rates as well as the ratio of the flow rates of the polar solvent to the hydrocarbon solvent are regulated such that the essential part of the butenes will be entrained by the hydrocarbon solvent and the essential part of the butadiene is entrained by the polar solvent.

The butenes/hydrocarbon mixture obtained overhead from the first extraction column is then treated in a first distillation column in order to obtain the butenes effluent overhead and the hydrocarbon solvent from the bottom which may be recycled.

The butadiene/polar solvent mixture is then supplied to the head of a second liquid-liquid extraction column in which the butadiene is extracted from the polar solvent by bringing it into direct contact with a quantity of hydrocarbon solvent that is larger than in the first liquid-liquid extraction column, which is introduced into the bottom of said second liquid-liquid extraction column.

The butadiene/hydrocarbon mixture obtained from the head of the second liquid-liquid extraction column is then treated in a distillation column in order to obtain a purified butadiene effluent overhead and the hydrocarbon solvent from the bottom which may be recycled.

Preferably, the liquid-liquid extraction columns of said butadiene/butenes separation section are operated at a pressure in the range 0.1 to 1 MPa, and at a temperature in the range 20° C. to 60° C.

In another embodiment of the invention, said step D3) comprises at least one distillation step and an extractive distillation step. The distillation step may be carried out upstream or downstream of the extractive distillation step. In a non-limiting manner, the extractive distillation may be carried out with a solvent such as N-methyl pyrrolidone, dimethylformamide or acetonitrile.

The various treatment steps for purification of butadiene, D1), D2), D2bis) and D3), may clearly be used to co-treat any stream comprising butadiene which may be produced by other processes located in the proximity of the process of the invention.

Effluent Treatment Step E1)

In accordance with the invention, step E1) for the treatment of effluents is supplied with at least the water/ethanol/acetaldehyde raffinate obtained from step E2) and produces at least one ethanol-rich effluent, an acetaldehyde-rich effluent and a water-rich effluent. If the spent water effluent obtained from step D2) or the alcohol-containing water effluent obtained from step F) or the spent water effluent obtained from step C2) have not undergone step E2) for the elimination of impurities and brown oils, they may be supplied directly to step E1) for the treatment of effluents. Section E1) is advantageously also supplied with a fraction of the ethanol feed.

Preferably, and as a distinction from the prior art, no ethanol- or acetaldehyde-losing withdrawal is carried out.

Preferably, said step E1) comprises at least two distillation sections, a "water and ethanol" distillation section and an "acetaldehyde" distillation section.

Said water/ethanol/acetaldehyde effluent obtained from step E2) and optionally the spent water effluent obtained from step D2) supply said acetaldehyde distillation section in which the acetaldehyde is separated in a manner so as to form an effluent which is rich in acetaldehyde, the residue from said acetaldehyde distillation section supplying a water and ethanol distillation section in order to separate an overhead ethanol-rich effluent and a bottom water-rich effluent. The alcohol-containing water effluent obtained from step F) and the spent water effluent obtained from step C2) do not contain acetaldehyde, and so they can be used to supply said water and ethanol distillation section directly.

The ethanol-rich effluent obtained from step E1) is mainly constituted by ethanol. The term "mainly" means more than 80% by weight, preferably more than 84% by weight. In a non-limiting manner, the ethanol-rich effluent obtained from step E1) may contain impurities such as water, ethyl acetate, butanol and hexanol.

The impurities other than water represent less than 10%, preferably less than 5%, more preferably less than 2% by weight of the stream.

The acetaldehyde-rich effluent obtained from step E1) is mainly constituted by acetaldehyde and ethanol. The term "mainly" means more than 80% by weight, preferably more than 85% by weight. In a non-limiting manner, the acetaldehyde-rich effluent obtained from step E1) may contain impurities such as water, ethyl acetate or acetone. The impurities other than water represent less than 10%, preferably less than 5% by weight of the stream.

Said acetaldehyde-rich effluents, ethanol-rich effluents and water-rich effluents are then recycled to the remainder of the process of the invention. The fraction of said ethanol-rich effluent supplied to step A) is preferably at least 0.7, more preferably at least 0.75, highly preferably at least 0.8. The fraction of said water-rich effluent supplied to said step F) is advantageously in the range 0 to 0.3, highly advantageously in the range 0 to 0.1, more advantageously in the range 0 to 0.01. The fraction of said water-rich effluent supplied to said step E2) for the elimination of impurities and brown oils is advantageously in the range 0 to 1, preferably in the range 0.3 to 0.6, and advantageously in the range 0.4 to 0.5.

In another embodiment of the invention, said acetaldehyde-rich effluents, ethanol-rich effluents and water-rich effluents undergo a purification step before being recycled to the remainder of the process. The term "purification" means bringing said effluents into contact with adsorbents such as activated carbon, silica, alumina or a functionalized polymeric resin, for example. As an example, an activated carbon can be used to eliminate traces of butanol and hexanol comprised in the ethanol-rich stream. As an example, a basic resin may be used to eliminate acetic acid present in the water-rich effluent. When the adsorbents are saturated, and cannot guarantee the purity of the acetaldehyde-rich effluents, ethanol-rich effluents and water-rich effluents, they are either eliminated or regenerated for re-use.

Step E2) for Elimination of Liquid Impurities and Brown Oils

In accordance with the invention, a step E2) for elimination of impurities and brown oils is supplied with at least the ethanol/acetaldehyde/water effluent obtained from step D1) and with a fraction of the water effluent obtained from step E1) and produces at least one ethanol/acetaldehyde/water raffinate, a light brown oil effluent and a heavy brown oil effluent.

Preferably, said step E2) comprises at least one scrubbing/back-scrubbing section, a section for distilling light brown oils, and a section for distilling heavy brown oils.

Said preferred scrubbing/back-scrubbing section is supplied with said ethanol/acetaldehyde/water effluent obtained from step D1) to an intermediate point, advantageously as a mixture with the spent water effluent obtained from step D2), the alcohol-containing water effluent obtained from step F) and the spent water effluent obtained from step C2), if this latter step is carried out, and preferably as a mixture with a fraction of the spent water effluent obtained from step D2). These effluents are more water-rich than the ethanol/acetaldehyde/water effluent obtained from step D1), and so introducing them as a mixture means that the hydrocarbon losses in the raffinate can be limited.

The bottom of said preferred scrubbing/back-scrubbing section is supplied with a hydrocarbon effluent and the head is supplied with a fraction of the water effluent obtained from step E1), which does not comprise ethanol and acetaldehyde. The hydrocarbon effluent and the fraction of the water effluent obtained from step E1) are supplied at a temperature which is preferably in the range 10° C. to 70° C., more preferably in the range 45° C. to 55° C. Said scrubbing/back-scrubbing section produces a hydrocarbon scrub extract overhead which is loaded with a fraction of the impurities and brown oils, and said ethanol/acetaldehyde/water raffinate from the bottom.

Said scrubbing/back-scrubbing section is preferably operated at a pressure in the range 0.1 to 0.5 MPa, preferably in the range 0.2 to 0.4 MPa. Preferably, the water added to carry out the back-scrubbing is such that the water content in the water/ethanol/acetaldehyde raffinate is more than 30% by weight, preferably more than 40% by weight.

In one embodiment, the contact between the two liquid phases in said scrubbing/back-scrubbing section is carried out in a liquid-liquid extractor. Various modes of contact may be envisaged. Non-limiting examples that may be cited are a packed column, a pulsed column or an agitated compartmented column. In another embodiment, contact between the two liquid phases in said scrubbing/back-scrubbing section is carried out in a membrane contactor, or a cascade of membrane contactors. This contact mode is particularly suited to the system being used. In fact, water-ethanol-hydrocarbon mixtures are known to form stable emulsions, which may be problematic in a liquid-liquid extractor. The membrane contactor can be used to generate a large contact area, promoting the transfer of impurities and oils towards the hydrocarbon phase without generating an emulsion.

Said hydrocarbon scrub extract is supplied to said light brown oils distillation section, which produces said light brown oil effluent as a distillate and a hydrocarbon residue comprising the heavy fraction of the brown oils.

Said light brown oil effluent is composed of impurities produced by the reaction step B), principally diethyl ether, ethyl acetate and crotonaldehyde, but also the light fraction of the brown oils, composed of impurities in smaller quantities, including pentene, isoprene, butanal and vinyl ethyl ether. This effluent may be burned off to provide a portion of the heat necessary for the hot oil circuit or for the steam boilers of the process, or distilled to recover a diethyl ether effluent and/or an ethyl acetate/crotonaldehyde effluent, which could be either upgraded or recycled to the reaction section of step B) for re-transformation.

Said hydrocarbon residue essentially contains the hydrocarbons used for scrubbing, but also the heaviest fraction of the brown oils. In order to prevent the brown oils from accumulating by recycling the hydrocarbon effluent to the liquid-liquid extractor, a fraction of said hydrocarbon residue is treated in said heavy oils distillation section, consisting of a distillation column, which produces a hydrocarbon distillate essentially composed of hydrocarbons still with a few traces of brown oils and, as a residue, said heavy brown oils effluent comprising more than 80%, preferably more than 85% of hydrocarbons as well as the heaviest brown oils. The fraction of said hydrocarbon effluent sent to said distillation section for the oils is in the range 5% to 30% of the total flow rate of said hydrocarbon residue and preferably in the range 10% to 20%. The hydrocarbon distillate is mixed with the fraction of hydrocarbon residue which has not been treated in said heavy oils distillation section in order to form the hydrocarbon effluent supplied to said scrubbing/back-scrubbing section.

This effluent, which preferably represents in the range 0.1% to 20% of the feed for said heavy oils distillation section, preferably in the range 0.3% to 5%, may be burned off in order to provide a portion of the heat necessary for the hot oil circuit or the steam boilers of the process. A makeup of hydrocarbons equivalent to the losses at the bottom of said heavy oils distillation section is necessary in order to keep the scrubbing flow rate constant. This column is regulated so as to keep the concentration of brown oils in the hydrocarbon recycle loop constant (hydrocarbon effluent/scrubbing hydrocarbon effluent loop).

The light and heavy brown oils are eliminated from the process.

The ethanol/acetaldehyde/water effluent obtained from step D1) principally comprises ethanol, acetaldehyde, water but also impurities such as diethyl ether, ethyl acetate and brown oils as defined above. These impurities can accumulate if they are returned to the reaction steps A) and B) within the acetaldehyde-rich distillation cut and/or the ethanol-rich distillation cut and if they are only partially converted in the reaction sections of steps A) and B). Step E2) can be used to recover a portion of these impurities before the effluent treatment step E1), which means that demixing of the brown oils in the distillation columns can be avoided, the distillation layout can be simplified, and an ethanol effluent, an acetaldehyde effluent and a water effluent with a greater purity than in the prior art may be obtained.

Scrubbing the ethanol/acetaldehyde/water effluent obtained from step D1) with a hydrocarbon effluent entrains some impurities, while back-scrubbing the hydrocarbon stream entrains a portion of the impurities and the brown oils with a water effluent fraction obtained from step E1), in a manner such as to limit any loss of acetaldehyde and ethanol.

Surprisingly, the Applicant has discovered that it is possible to obtain a liquid-liquid phase separation by adding certain hydrocarbons to the ethanol/acetaldehyde residue obtained from step D1). This result is surprising, as the ethanol/acetaldehyde residue obtained from the step is very rich in ethanol and acetaldehyde which are miscible with hydrocarbons in any proportions. By suitable selection of the hydrocarbon, the Applicant has discovered that it is possible to obtain liquid-liquid phase separation, and thus to carry out a liquid-liquid extraction in order to eliminate a portion of the impurities contained in the ethanol/acetaldehyde/water effluent obtained from step D1). Said hydrocarbon effluent may contain saturated and/or unsaturated and/or aromatic hydrocarbons, preferably saturated hydrocarbons. Said hydrocarbon effluent is advantageously constituted by a mixture of hydrocarbons containing 6 to 40 carbon atoms, preferably in the range 10 to 20 carbon atoms. In a non-limiting manner, said hydrocarbon effluent may be a gas oil cut or desulphurized kerosene cut or alternatively a hydrocarbon cut produced by a Fischer-Tropsch type unit.

Adding water to the scrubbing/back-scrubbing section means that better operation of the process for elimination of the impurities and brown oils in accordance with the invention can be obtained.

Thus, the process of the invention avoids regularly purging ethanol in order to prevent the accumulation of brown oils, which means that the overall performances of the process are improved.

Step F) for Scrubbing Gaseous By-Products with Water

In accordance with the invention, a step F) for scrubbing with water is supplied with the effluent of gaseous by-products obtained from step D1) as well as with a fraction of the water-rich effluent obtained from said step E1), and produces at least one alcohol-containing water effluent.

The aim of said step F) is to recover the small fraction of ethanol entrained in said effluent of gaseous by-products obtained from step D1) in order to improve the overall yield of the process.

The quantity of water obtained from said step E1) which is necessary in said step F) of the invention is very low, in contrast to that necessary in the prior art, because the effluent vapour obtained from step B) has been scrubbed with an ethanol stream containing little or no acetaldehyde in step D1). Thus, only a small fraction of ethanol remains in this stream, which is readily recovered with a small quantity of water compared with the quantity of water which would have been necessary if there had been traces of acetaldehyde in the effluent of gaseous by-products obtained from step D1).

The ethanol-charged water following scrubbing is withdrawn from said step F) and constitutes the alcohol-containing water effluent. It is preferably supplied to step E1), directly to the water-ethanol distillation section without overloading the acetaldehyde distillation section. In another embodiment of the invention, it is preferably supplied to step E2) for the elimination of impurities and brown oils.

Thus, the process of the invention can be used to minimize the flow rate of effluents to be treated in the effluent treatment step. It can also be used to reduce the losses of butadiene as far as possible, allowing more than 98%, preferably more than 99% of the butadiene produced at the end of the reaction steps to be recovered in said purified butadiene effluent.

Figure 2:
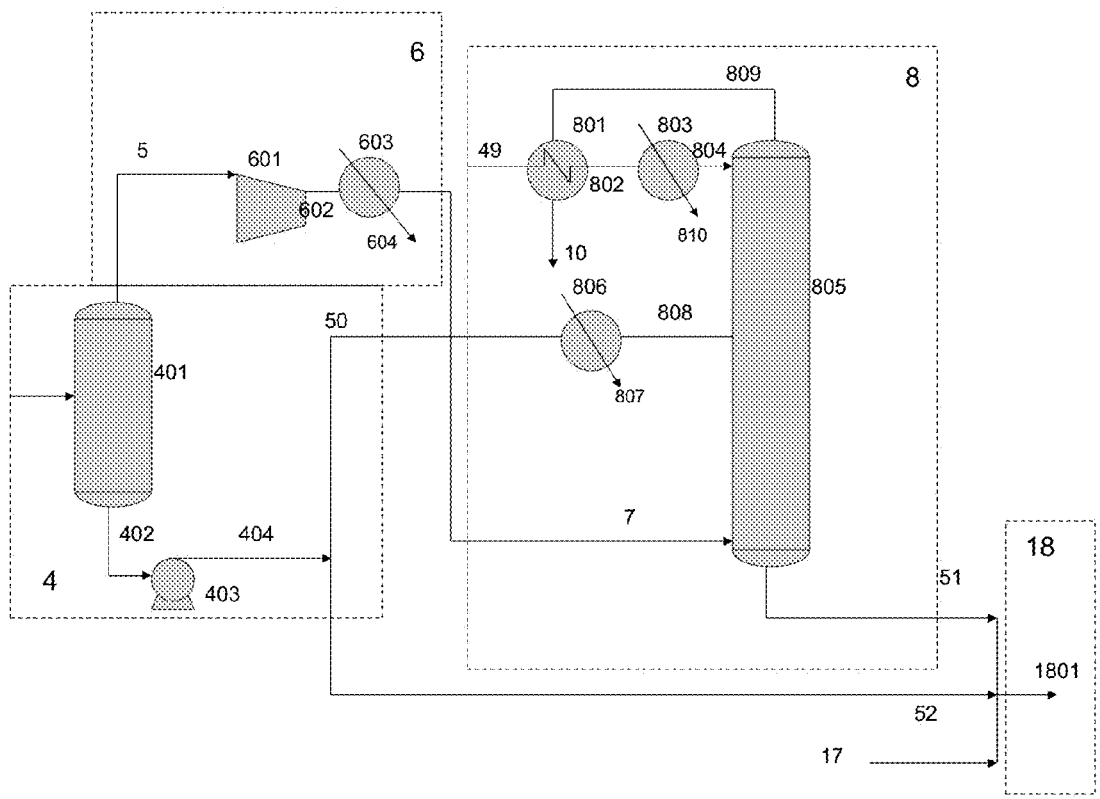

This assembly is described in more detail in FIG. 2.

Figure 3:
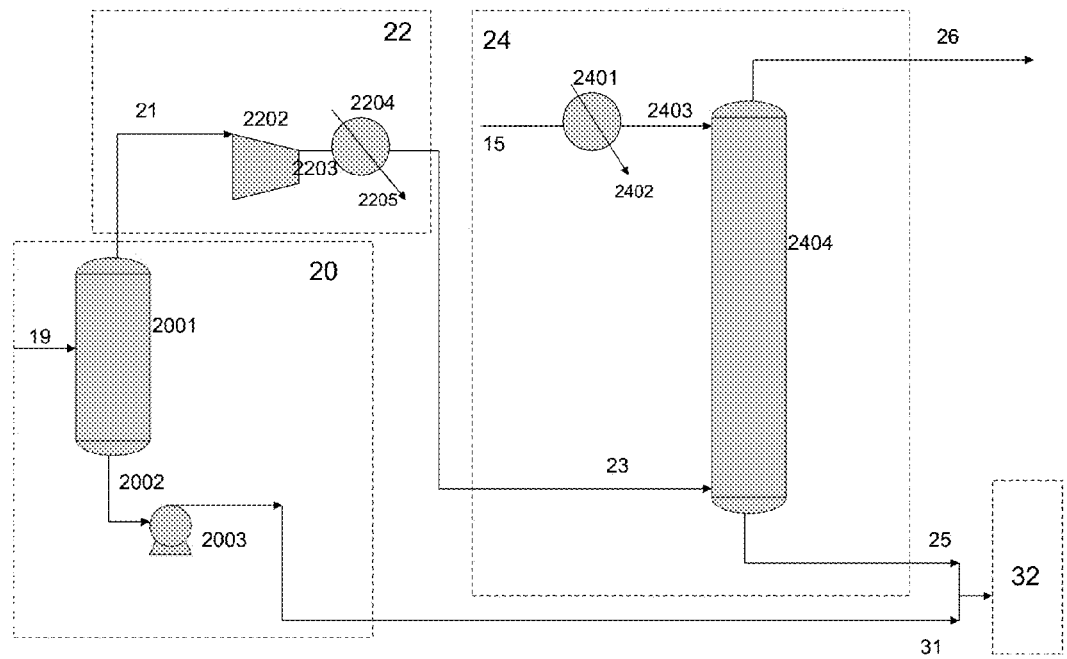

FIG. 3 diagrammatically shows, in a non-limiting manner, separation of the effluent form the reaction section.

Figure 4:
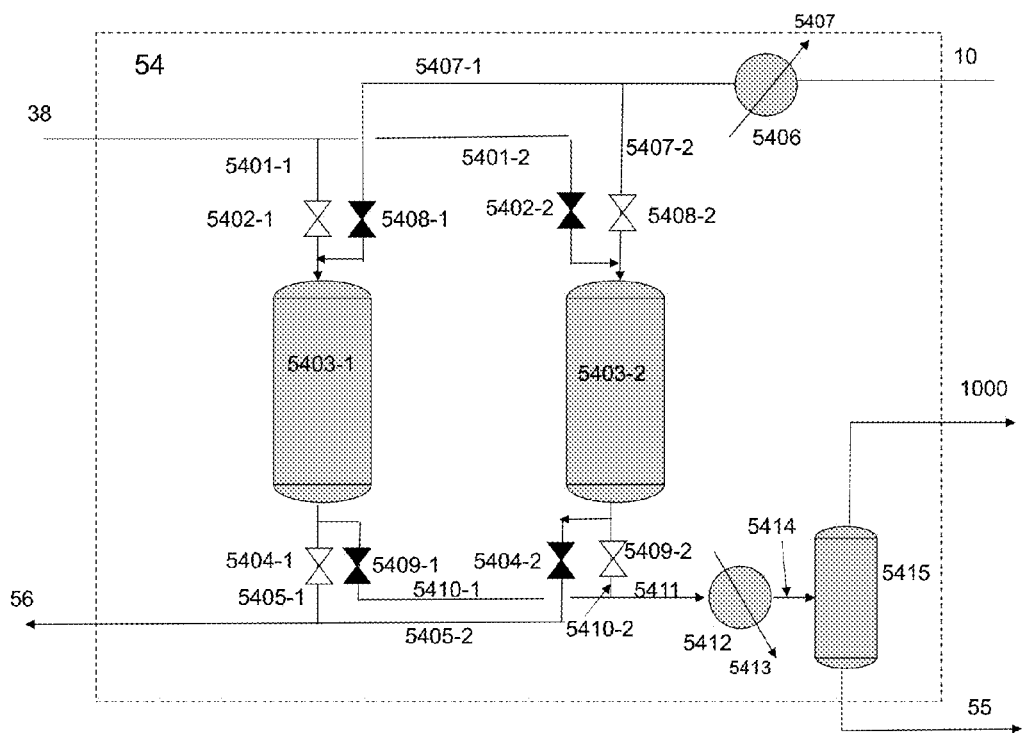

FIG. 4 shows the sieve drying of butadiene in a diagrammatic and non-limiting manner.

Figure 5:
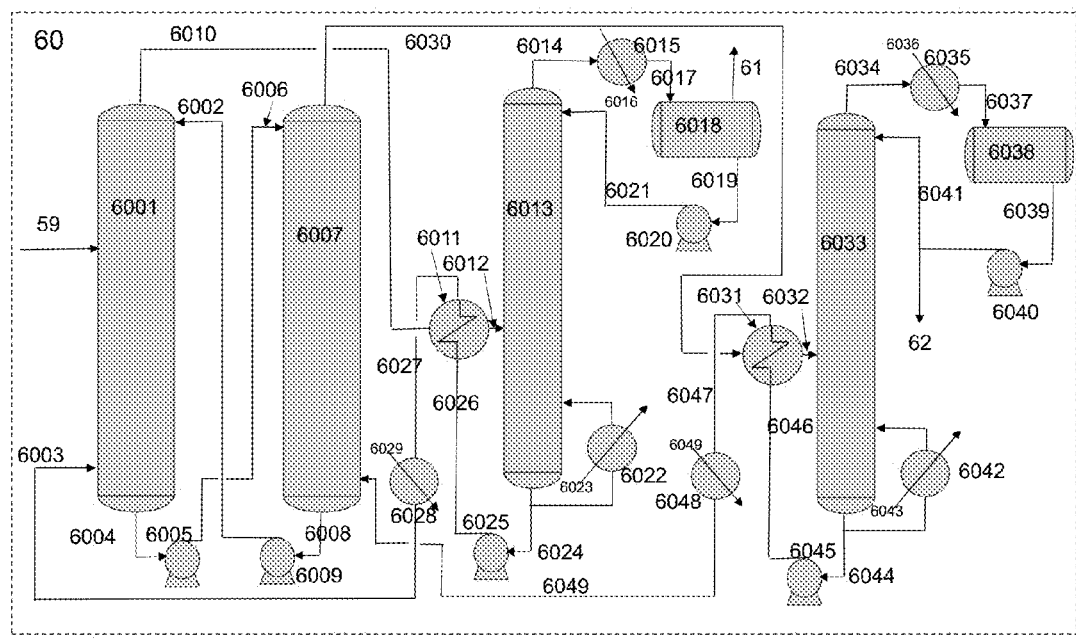

FIG. 5 shows, in a diagrammatic and non-limiting manner, the purification of butadiene using a polar solvent.

Figure 6:
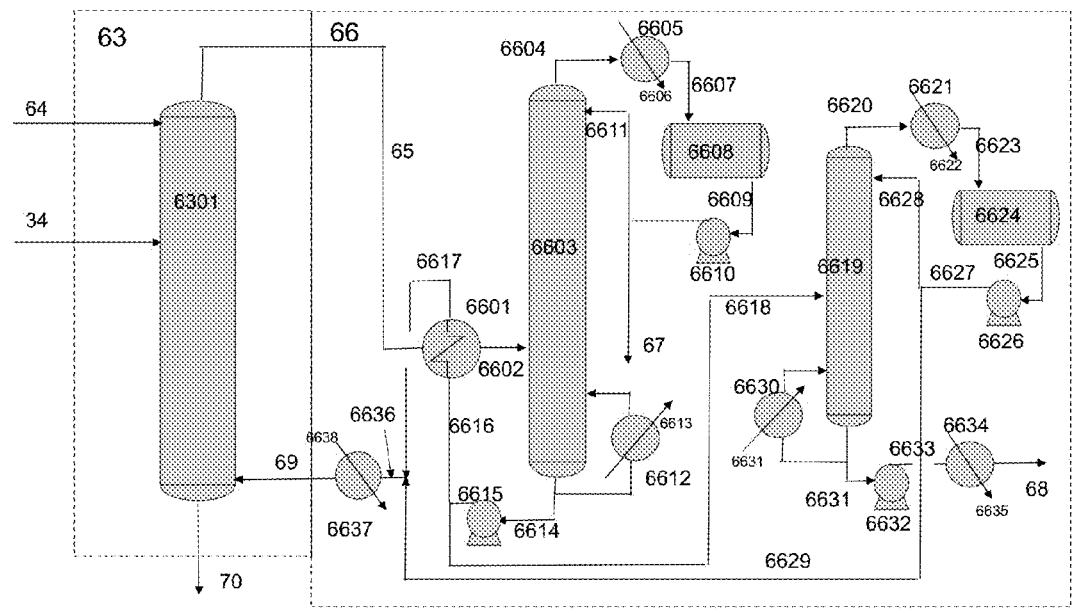

FIG. 6 shows, in a diagrammatic and non-limiting manner, the extraction of less polar impurities and brown oils by scrubbing/back-scrubbing.

Figure 7:
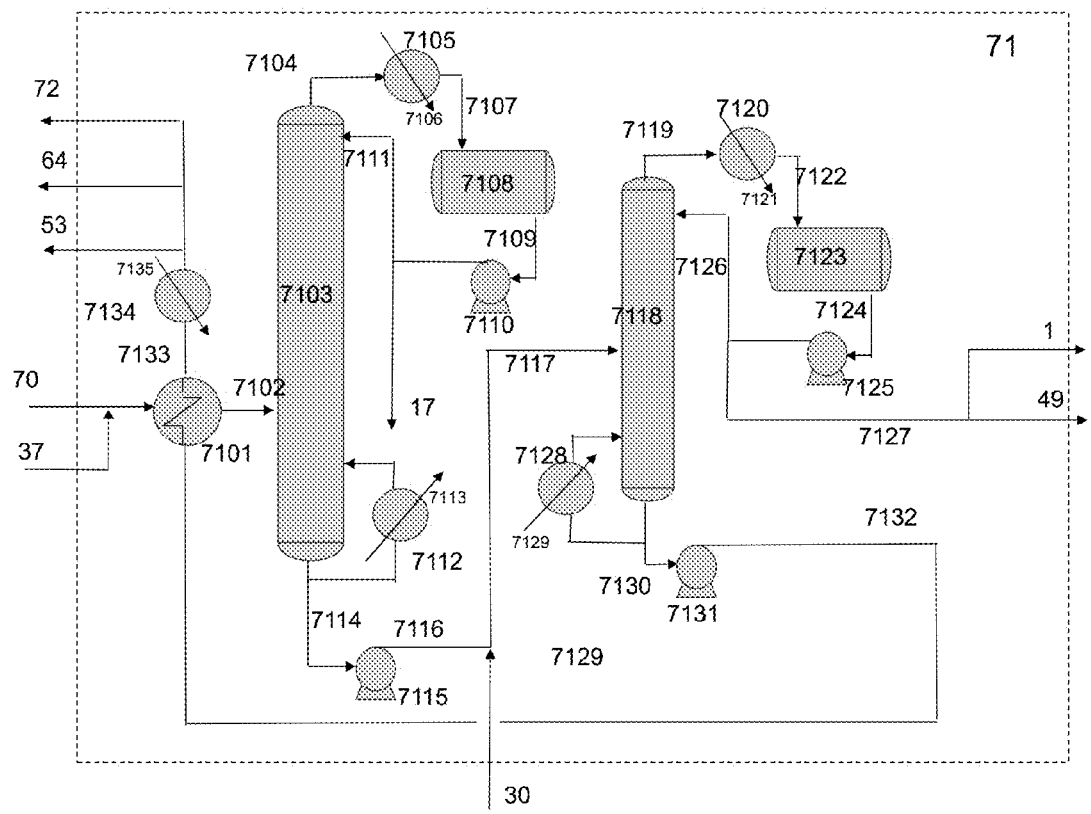

FIG. 7 presents a possible arrangement for the distillation section.

Figure 1:
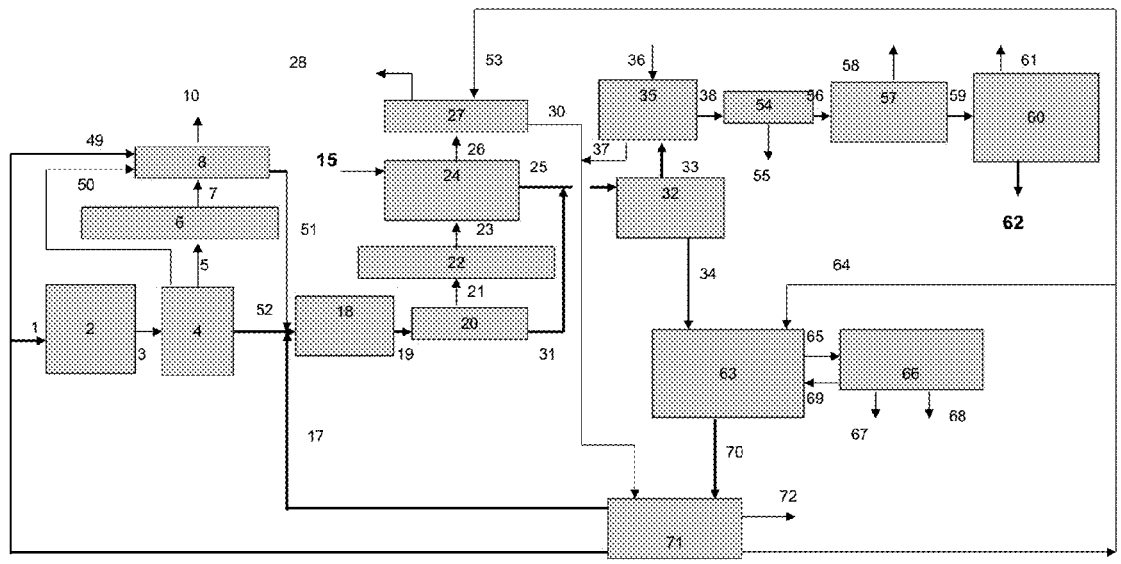
FIG. 1 shows, in a diagrammatic and non-limiting manner, and arrangement of the process of the invention.

FIG. 1 shows, in a diagrammatic and non-limiting manner, an arrangement of the process of the invention.

A fraction of the ethanol effluent obtained from the distillation section 71 is sent via the conduit 1 to the reaction section 2, where a portion of the ethanol is converted principally into acetaldehyde and into hydrogen. The effluent from said reaction section is sent to the separation section 4 via the conduit 3.

The separation section 4 can be used to separate a hydrogen effluent 5 compressed in section 6, and an ethanol/acetaldehyde effluent, which is separated into two fractions, one being supplied via the conduit 52 to the reaction section 18, the other being sent to the scrubbing section 8 via the conduit 50 in order to scrub the compressed hydrogen effluent 7. The compressed hydrogen effluent is also scrubbed with a fraction of the ethanol effluent 49 obtained from the distillation section 71 and evacuated as a purified hydrogen effluent via the conduit 10. This assembly is described in more detail in FIG. 2.

The reaction section 18 is supplied with the acetaldehyde effluent obtained from the distillation section 71 via the conduit 17, by the ethanol/acetaldehyde effluent which has been used for scrubbing the hydrogen arriving via the conduit 51, and by the ethanol/acetaldehyde effluent supplied via the conduit 52 from the separation section 4. The effluent from the reaction section 18 is sent to the separation section 20 via the conduit 19 to be separated into a gaseous effluent 21 and a liquid effluent 31.

The gaseous effluent 21 is compressed in the section 22. It is supplied, via the conduit 23, to a scrubbing section 24 in which it is scrubbed by contact with the ethanol feed 15. This ensemble is described in more detail in FIG. 3. The compressed and scrubbed gaseous effluent is supplied to a water scrubbing section 27 via the conduit 26, in which section it is scrubbed with a fraction of the water effluent 53 obtained from the distillation section 71. The water charged with ethanol after scrubbing is returned to the distillation section 71 via the conduit 30, directly to the water-ethanol separation column without overloading the acetaldehyde column. The vapour effluent scrubbed in section 27 is withdrawn via the conduit 28.

The liquid effluent obtained from the separator 20, sent via the conduit 31, is mixed with the bottom scrubbing liquid 24 arriving via the conduit 25. The mixture is sent to the distillation section 32 which will separate an overhead butadiene cut and a mixture comprising water, ethanol, acetaldehyde and impurities from the bottom. The butadiene cut is sent via the conduit 33 to a water scrub 35 intended to eliminate polar impurities and especially acetaldehyde. The scrubbing water, which is clean water, is introduced via the conduit 36. Water charged with acetaldehyde is returned to the distillation section 71 via the conduit 37.

The pre-purified butadiene effluent is sent to a drying section 54 via the conduit 38 in order to eliminate all traces of water. The dry butadiene effluent 56 is supplied to a cryogenic distillation 57 and water is evacuated via the conduit 55. This assembly is described in more detail in FIG. 4. The light products leave the cryogenic distillation section overhead at −35° C. via the conduit 58, with a very small loss of butadiene. The topped butadiene cut leaves via the conduit 59 and arrives in a liquid-liquid extraction section 60. The function of this extraction is described in more detail in FIG. 5.

The purified butadiene effluent leaves this extraction step via the conduit 62, and has a purity that satisfies current specifications (more than 99.5%), the residual impurities being principally butenes. The butenes separated in this section (comprising a small quantity of butadiene) leave the unit via the conduit 61.

The ethanol/acetaldehyde residue from the bottom of the distillation step 32 is sent via the conduit 34 to the scrubbing/back-scrubbing section 63, heavy hydrocarbons being supplied via the conduit 69 and recycled water being supplied via the conduit 64. The heavy scrubbing hydrocarbons, charged with impurities, leave via the conduit 65 and supply the regeneration section 66, from which heavy hydrocarbons leave at 69 and return to the scrub, and a light fraction 67 is removed, in particular containing diethyl ether and ethyl acetate, plus some light brown oils. A heavy cut 68 is also removed, containing heavy brown oils and a small portion of the scrubbing hydrocarbons. The function of sections 63 and 66 is described in more detail in FIG. 6.

The bottom liquid from the scrubbing/back-scrubbing section 63, containing both the ethanol/acetaldehyde residue 34 freed from its impurities and with high affinities for the heavy hydrocarbons 69 and the scrubbing water 64, and is sent to the distillation section 71 via the conduit 70. This section can be used to separate an acetaldehyde fraction returned to the reaction section 18 via the conduit 17, an ethanol fraction a portion of which is sent to the reaction section 2 via the conduit 1 and a portion of which is sent to the scrubbing step 8 via the conduit 49, and a water fraction containing a little acetic acid, which is partially recycled to the scrubbing step 27 via the conduit 53 and the scrubbing step 63 via the conduit 64, the remainder of the water being purged from the unit via the conduit 72. The function of this section is described in detail in FIG. 7.

FIG. 2 shows, in a diagrammatic and non-limiting manner, the separation of the effluent from the reaction section 2 and the hydrogen treatment step.

The effluent from the reaction section 2 is supplied via the conduit 3 to a chamber 401 for separating a hydrogen effluent 5 and a liquid phase 402. The hydrogen effluent 5 is compressed by the compressor 601. The compressed hydrogen effluent is then sent via the conduit 602 to a heat exchanger 603 which will cool the gas with the aid of a cooling utility 604. The compressed hydrogen effluent leaves the heat exchanger 603 via the conduit 7 and enters the bottom of the adiabatic scrubbing column 805 and will be scrubbed with two liquids cooled to low temperature.

The liquid phase 402 is pumped up via the pump 403 to a higher pressure in order to form the ethanol/acetaldehyde effluent 404. The fraction of the ethanol/acetaldehyde effluent 50 is cooled via the heat exchanger 806 with the aid of a coolant 807 which may be propane, for example. The liquid leaves 806 via the conduit 808 before entering the column 805 at an intermediate level between the head and bottom of the column.

The fraction of ethanol effluent obtained from the distillation section 71 is supplied to a first heat exchanger 801 via the conduit 49, allowing the ethanol at 49 to be cooled and to reheat the hydrogen leaving the column 805 via the conduit 809. At the outlet from this exchanger, the purified hydrogen effluent, which has been reheated, exits the process via the conduit 10 and the cooled ethanol is sent via the conduit 802 to the exchanger 803 to cool it further with the aid of a coolant 810 which may be propane, for example. The ethanol is sent to the column 805 via the conduit 804. The liquid column bottom effluent 805 is sent to the reaction section 18 via the conduit 51 as a mixture with the fraction 52 of the ethanol/acetaldehyde effluent 404.

FIG. 3 diagrammatically shows, in a non-limiting manner, separation of the effluent from the reaction section 18 and a portion of the butadiene effluent treatment step.

The effluent 19 from the reaction section 18 is supplied to a separator 2001 in which a butadiene effluent 21 and a liquid phase 2002 are separated. The butadiene effluent 21 is compressed in a compressor 2202, the compressed vapour effluent 2203 then being cooled in a heat exchanger 2204 by a cooling utility 2205.

The compressed and cooled vapour effluent 23 is supplied to the adiabatic scrubbing column 2404 where it will be scrubbed with the ethanol feed 15, which has already been cooled in the heat exchanger 2401 by a coolant arriving via the conduit 2402. The pre-cooled ethanol feed enters the column 2404 via the conduit 2403. A vapour effluent 26 which has been compressed and scrubbed is recovered overhead and the scrubbing liquid 25 is recovered from the bottom.

The bottom scrubbing liquid 25 is mixed with the liquid phase 2002 which has already been pumped via the pump 2003 and is brought in via the conduit 31. The mixture of 25 and 31 contains all of the butadiene produced, and is sent to the section 32.

FIG. 4 shows the sieve drying of butadiene in a diagrammatic and non-limiting manner.

The pre-purified butadiene effluent arrives for drying via the conduit 38; it passes through the open valve 5402-1 or 2 then the drying sieve contained in the chamber 5403-1 or 2. The dry butadiene leaves the chamber 5403-1 or 2 through the open valve 5404-1 or 2, then the conduit 5405-1 or 2 and finally is sent to the cryogenic distillation step via the conduit 56.

The stream of hydrogen arrives via the conduit 10 and is heated in the heat exchanger 5406 by exchange with a heating means 5407 which may be hot oil, for example.

At the outlet from the heat exchanger 5406, the hot hydrogen stream is sent via the conduit 5407-2 or 5407-1 to the open valve 5408-2 or 1, and from this to the regeneration chamber 5403-2 or 1. At the outlet from the chamber 5403-2 or 1, the hot gas charged with water passes via the open valve 5409-2 or 1 then via the conduit 5410-2 or 1, the conduit 5411, then the heat exchanger 5412 where it is cooled and the water is condensed with the aid of cooling water arriving via the conduit 5413. The gas may equally be cooled by an air cooler. The cooled gas leaving 5412 is sent through the conduit 5414 to the separator 5415 where the condensed water is separated and sent out of the unit via the conduit 55. The condensed water contains a portion of the ethanol contained in the stream 10; it may optionally be sent to the section 71 for recovering ethanol.

FIG. 5 shows, in a diagrammatic and non-limiting manner, the purification of butadiene using a polar solvent, for example DMSO (dimethylsulphoxide).

The dry butadiene effluent is supplied to a first extraction column 6001 via the conduit 59, into which a stream of polar solvent which may, for example, be DMSO, arrives overhead via the conduit 6002. At the bottom, a hydrocarbon solvent such as a pentane or cyclohexane is supplied via the conduit 6003.

At the bottom of the column 6001, the polar solvent and the dissolved butadiene leave via the conduit 6004, are pumped by the pump 6005, and are sent to the head of the column 6007 via the conduit 6006. A large quantity of hydrocarbon solvent is injected into the bottom of the column 6007 via the conduit 6049 in order to separate the butadiene from the polar solvent. At the bottom of 6007, the polar solvent, free of butadiene, leaves via the conduit 6008 and is pumped via the pump 6009 then returned to the column 6001 via the conduit 6002.

At the column head, the butadiene dissolved in the hydrocarbons is sent to the heat exchanger 6031 via the conduit 6030, where it is heated by indirect exchange with the bottom of the column 6033. At the outlet from the heat exchanger 6031, the butadiene-solvent mixture is supplied to the column 6033 via the conduit 6032.

This column 6033 is provided with a device 6042 for heating and reboiling the bottom of the column using a heating means 6043 which may be low pressure steam, for example. At the column head, the overhead vapour leaving via the conduit 6034 is cooled and completely condensed in the heat exchanger 6035, using a cooling utility 6036. At the outlet from the heat exchanger 6035, the condensed liquid flows into the chamber 6038 via the conduit 6037. The liquid is then sent towards the pump 6040 via the conduit 6039. A portion of the liquid is sent as a reflux to the column 6033 via the conduit 6041, the remainder, which constitutes the purified butadiene effluent, is sent out of the process via the conduit 62.

The bottom of the column 6033, which is a hydrocarbon solvent, is sent to the pump 6045 via the conduit 6044. At the outlet from the pump 6045, the solvent is sent to a heat exchanger 6031 via the conduit 6046, where it is cooled by indirect heat exchange with the feed for the column 6033. At the outlet from the heat exchanger 6031, the solvent is sent to the heat exchanger 6048 via the conduit 6047, to finish cooling using a cooling utility 6049. At the outlet from the exchanger 6048, the solvent is returned to the scrubbing column 6007 via the conduit 6049.

A mixture of hydrocarbon solvent and butenes leaves the column 6001 overhead, with a small loss of butadiene. This mixture is sent to the heat exchanger 6011, where it is heated by indirect exchange with the bottom of the column 6013. At the outlet from the heat exchanger 6011, the butene-solvent mixture supplies the column 6013 via the conduit 6012. This column 6013 is provided with a device 6022 which can be used to heat and reboil the bottom of the column using a heating means 6023 which may be low pressure steam, for example. At the column head, the overhead vapour leaving via the conduit 6014 is cooled and completely condensed in the heat exchanger 6015, using a cooling utility 6016. At the outlet from the heat exchanger 6015, the partially condensed mixture is supplied to the chamber 6018 via the conduit 6017. The gas and liquid phases are separated in this chamber 6018. The liquid phase from the chamber is sent to the pump 6020 via the conduit 6019, then sent as a reflux to the column 6013 via the conduit 6021. The vapour phase, essentially constituted by butenes and a little butadiene, is removed from the process via the conduit 61 to act as a fuel, for example.

The bottom of the column 6013, which is a hydrocarbon solvent, is sent to the pump 6025 via the conduit 6024. At the outlet from the pump 6025, the solvent is sent via the conduit 6026 to the heat exchanger 6011, where it is cooled by indirect heat exchange with the feed for the column 6013. At the outlet from the heat exchanger 6011, the solvent is sent via the conduit 6027 to the heat exchanger 6028, to finish cooling using a cooling utility 6029. At the outlet from the exchanger 6028, the solvent is returned to the scrubbing column 6001 via the conduit 6003.

FIG. 6 shows, in a diagrammatic and non-limiting manner, the extraction of less polar impurities and brown oils by scrubbing/back-scrubbing.

The ethanol/acetaldehyde residue 34 is supplied to the scrubbing column 6301. The heavy hydrocarbon solvent (which may, for example, be a gas oil cut or desulphurized kerosene, or a cut produced by a Fischer-Tropsch type unit), is supplied to the bottom of the column 6301 via the conduit 69, while a fraction of the water effluent 64 supplies the column 6301 overhead.

The heavy scrubbing hydrocarbon effluent is withdrawn overhead from the column 6301 via the conduit 65 and sent to the section 66 for regeneration. It is preheated in the heat exchanger 6601 by exchange with the bottom of the column 6603. At the outlet from the exchanger 6601, the preheated heavy scrubbing hydrocarbon effluent is sent to the column 6603 via the conduit 6602.

This column 6603 is provided with a device 6612 in order to heat and reboil the bottom of the column using a heating means 6613 which may be hot oil, for example. At the column head, the overhead vapour leaving via the conduit 6604 is cooled and completely condensed in the heat exchanger 6605, using a cooling utility 6606. At the outlet from the heat exchanger 6605, the condensed liquid flows into the chamber 6608 via the conduit 6607. The liquid is then sent via the conduit 6609 to the pump 6610. A portion of the liquid is sent via the conduit 6611 to the column 6603 as a reflux; the remainder is sent out of the unit via the conduit 67.

The column bottom 6603 is sent to the pump 6615 via the conduit 6614. A fraction of the liquid leaving the pump 6615 is sent to another distillation column 6619 via the conduit 6618. The remaining fraction is sent to the heat exchanger 6601 via the conduit 6616, and can be used to cool the bottom liquid 6616 by indirect exchange with the feed 65 for the column 6603. The cooled bottom liquid leaves the exchanger 6601 via the conduit 6617 for sending to the heat exchanger 6637.

The purification column 6619 is provided with a device 6630 in order to heat and reboil the column bottom using a heating means 6631 which may be hot oil, for example. At the column head, the overhead vapour leaving via the conduit 6620 is cooled and completely condensed in the heat exchanger 6621, using a cooling utility 6622. At the outlet from the heat exchanger 6621, the condensed liquid flows into the chamber 6624 via the conduit 6623. The liquid is then sent to the pump 6626 via the conduit 6625. A portion of the liquid is sent via the conduit 6628 to the column 6619 as a reflux, the remainder being sent to the exchanger 6637 via the conduit 6629 as a mixture with the column bottom 6603 where it is cooled using a cooling utility 6638. The hydrocarbons leaving 6637 are sent to the scrubbing column 6301 via the conduit 69.

The column head 6619 is essentially composed of heavy hydrocarbons still with a few traces of "black oil". An equivalent makeup of heavy hydrocarbons (not shown) is necessary to keep the scrubbing flow rate constant.

The liquid from the bottom of the column 6619 is removed via the conduit 6631 and is pumped via the pump 6632 then sent via the conduit 6633 to a heat exchanger 6634, where it is cooled by a fluid 6635, to be removed from the process via the conduit 68. It can then act as a fuel, for example. The fluid 6635 may be cooling water; it is also possible to use air with an air cooler, or to use a stream from the unit which has to be reheated as this fluid 6635.

FIG. 7 presents a possible arrangement for the distillation section 71.

The ethanol/acetaldehyde/water/polar impurities mixture obtained from scrubbing 63 is supplied to the distillation section 71 via the conduit 70. This stream is mixed with the scrubbing water charged with acetaldehyde arriving from the scrubbing section 35 via the conduit 37. The mixture of these two streams is heated by indirect heat exchange against the stream 7133 in the heat exchanger 7101. The output from this exchanger is supplied to the column 7103 via the conduit 7102. The column head leaving via the conduit 7104 is completely condensed in the heat exchanger 7105 by exchange with a cooling utility 7106. The exchanger output 7105 is supplied via the conduit 7107 to the reflux drum 7108. The liquid from this drum leaves via the conduit 7109 towards the pump 7110 which sends a reflux towards the column 7103 via the conduit 7111 and a distillate (acetaldehyde-rich effluent) towards the reaction section 18 via the conduit 17. This distillate principally contains acetaldehyde, but also water, ethanol and other light impurities (diethyl ether, butanal, acetone, ethyl acetate, etc).

Column 7103 is reboiled with the aid of the exchanger 7112 with low pressure steam arriving via the conduit 7113, for example. The product from the bottom of column 7103, principally containing water, ethanol, a little butanol, acetic acid and several other impurities, leaves via the conduit 7114 then is sent with the aid of the pump 7115 to the column 7118 via the conduit 7116. The scrubbing water from the scrubbing section 27, charged with ethanol, arrives via the conduit 30 and is mixed with the bottom product from 7103 arriving via the conduit 7116. The mixture is sent to the column 7118 via the conduit 7117.

The column head 7118 leaves via the conduit 7119 then is completely condensed via the heat exchanger 7120 with the aid of a cooling utility 7121. The outlet from the exchanger 7120 is supplied to the reflux drum 7123 via the conduit 7122. The liquid from this drum leaves via the conduit 7124 towards the pump 7125, which sends a reflux to the column 7118 via the conduit 7126 and a distillate via the conduit 7127, one portion towards the reaction section 2 via the conduit 1, the other portion towards the scrubbing 8 via the conduit 49 (ethanol-rich effluent). Adjustment of the ratio between these two destinations means that the ethanol/acetaldehyde ratio at the inlet to the reactor of section 18 can be adjusted. This distillate principally comprises ethanol, but also water, a little butanol, and several other impurities.

The column 7118 is reboiled with the aid of the exchanger 7128 with, for example, low pressure vapour arriving via the conduit 7129. The bottom product from the column 7118 (water-rich effluent), principally containing water and a little acetic acid, leaves via the conduit 7130 and is sent with the aid of the pump 7131 to the heat exchanger 7101 via the conduit 7132, where it is cooled by indirect exchange with the feed for the column 7103. The product is removed from 7101 via the conduit 7133 and is cooled in the exchanger 7134 with the aid of a cooling utility 7135. At the outlet from the exchanger, a portion of the water is sent via the conduit 64 to the scrubbing step 63 and via the conduit 53 to the scrubbing step 27; the remainder is purged out of the unit via the conduit 72.

EXAMPLES

The following examples are based on process simulations using stream recycles and integrating thermodynamic data based on experimental points (binary liquid-vapour equilibrium data and liquid-liquid distribution coefficient). In each of the examples, the flow rate of the feed was adjusted so as to obtain an annual production of 150 kt/year of a butadiene with a purity in the range 99.5% to 100% by weight (consistent with current use of the product), with an annual operating period for the process of 8000 h.

Example 1—Prior Art Butadiene Production Process 1.1—Hydrogen Treatment Step The gas phase at the outlet from the reactor for the conversion of ethanol into acetaldehyde, which represented a flow rate of 10 t/h, comprised hydrogen co-produced by the reaction, ethanol and acetaldehyde. It was important to limit as much as possible the losses of ethanol and acetaldehyde in order to maximize the overall yield of the process. Scrubbing the gas phase with water meant that 95.5% by weight of the acetaldehyde and ethanol contained in this gas phase could be recovered.

This scrubbing target was met using 50 t/h of water. This 50 tonne of water could be simply clean water, from outside the process, or be partly from water recycled from the process. The loss of ethanol in the purified hydrogen effluent was 31 kg/h.

Using recycled water meant that the consumption of clean water could be minimized but, due to the effect of recycling, would bring acetic acid into the purified hydrogen effluent. A maximum of 40 t/h of recycled water could be used. The consumption of "clean" water would thus be a minimum of 10 t/h. This 10 to 50 t/h of water represented between 35% and 70% of the flow of water treated in the whole of the prior art layout.

Whether or not the scrubbing water originated partially from recycled water or completely from clean water, the flow rate of the water entering the water/ethanol/acetaldehyde distillation section was raised to 142 t/h.

1.2—First Butadiene Separation Step, Alternative 1

The vapour effluent from the butadiene conversion step was compressed then scrubbed by bringing it into contact with the ethanol/acetaldehyde effluent obtained from the reactor for the conversion of ethanol to acetaldehyde, which had been cooled to 35° C. Scrubbing said vapour effluent using said ethanol/acetaldehyde effluent meant that almost all of the butadiene (99.988%) included in said vapour effluent before scrubbing could be recovered. The vapour effluent leaving the scrubbing step formed the scrubbed gas effluent. It comprised reaction by-products (ethylene, ethane, etc), but also ethanol and acetaldehyde.

Said scrubbed effluent gas was then scrubbed with recycled water to recover acetaldehyde and ethanol. It was necessary to use 12.7 t/h of water to recover all of the acetaldehyde and ethanol.

1.3—First Butadiene Separation Step, Alternative 2

This example differs from the preceding example in that the ethanol/acetaldehyde effluent obtained from the reactor for the conversion of ethanol into acetaldehyde was pre-cooled to 14° C. before being used to scrub the vapour effluent from the butadiene conversion step which had already been compressed.

The reduction in the temperature of the ethanol/acetaldehyde effluent meant that the whole of the butadiene included in said vapour effluent could be recovered and the quantity of ethanol and acetaldehyde entrained in the scrubbed gas effluent could be reduced.

This scrubbed gas effluent was then scrubbed with recycled water in order to recover acetaldehyde and ethanol. It was necessary to use 8.5 t/h of water to recover all of the acetaldehyde and ethanol.

Example 2—Process for the Production of Butadiene in Accordance with the Invention 2.1—Hydrogen Treatment Step After compression, the gas phase at the outlet from the reactor for the conversion of ethanol to acetaldehyde was scrubbed, with a fraction of the ethanol effluent obtained from the effluent treatment step. The scrubbed gas phase formed the purified hydrogen effluent. The loss of ethanol in the purified hydrogen effluent was 32 kg/h, similar to the loss of 31 kg/h of acetaldehyde in the prior art layout.

Scrubbing with recycled ethanol instead of water meant that the flow rate of water at the inlet to the water/ethanol/acetaldehyde distillation section could be reduced by 50 t/h, which was thus reduced to 91 t/h. This represents a saving of 35% in the flow rate of water moving in the whole of the process layout, and in particular in the columns of the distillation section. This saving resulted in a drop in the level of investment and consumption of utilities over the whole ethanol and acetaldehyde recovery section.

2.2—First Butadiene Separation Step, Alternative 1

In this example, the vapour effluent from the butadiene conversion step was compressed, then scrubbed by contact with the ethanol feed for the conversion process. The effluent gas leaving the scrubbing step formed the scrubbed gas effluent.

Said ethanol feed had the following composition: 93.3% by weight of ethanol and 6.7% of water, with no measurable traces of impurities. It was supplied to the scrubbing column at a temperature of 35° C. This scrub was used to recover 99.88% of the butadiene comprised in said vapour effluent. The scrubbed gas effluent was free of acetaldehyde, in contrast to the prior art examples.

The scrubbed gas effluent was then scrubbed with recycled water to recover the ethanol. It was necessary to use 3.2 t/h of water to recover all of the ethanol, i.e. much less than for the prior art examples.

2.3—First Butadiene Separation Step, Alternative 2

This example differs from the preceding example in that the ethanol feed was pre-cooled to 14° C. before being used to scrub the previously compressed vapour effluent from the butadiene conversion step. This scrubbing step was used to recover all of the butadiene included in said vapour effluent.

The scrubbed gas effluent, free of acetaldehyde, was then scrubbed with recycled water in order to recover the ethanol. It was necessary to use 0.4 t/h of water to recover all of the ethanol, i.e. more than 20 times less than in the prior art.

The reduction in the flow rate of water required for scrubbing meant that the flow rate of water at the inlet to the effluent treatment step could be reduced by 13%; as a consequence, this reduced the dimensions of the separation equipment and their energy consumption.

This advantageous variation of the invention using the ethanol feed in contrast to using a fraction of the ethanol effluent obtained from the effluent treatment step meant that the flow rate of the streams scrubbing the butadiene cut could be reduced. Thus, the ethanol flow rate was reduced by up to 16%.

2.4—First Butadiene Separation Step, Alternative 3

In this example, the vapour effluent from the butadiene conversion step was compressed, then scrubbed by contact with a fraction of the ethanol effluent obtained from the effluent treatment step. The gas effluent leaving the scrubbing step formed the scrubbed gas effluent.

Said ethanol effluent obtained from the effluent treatment step had the following composition: 84% by weight of ethanol and 16% by weight of water, with no measurable traces of impurities. It was supplied to the scrubbing column at a temperature of 35° C. This scrubbing step could be used to recover all of the butadiene comprised in said vapour effluent. The scrubbed gas effluent was free of acetaldehyde, in contrast to the prior art examples.

The scrubbed gas effluent was then scrubbed with recycled water in order to recover ethanol. It was necessary to use 2.8 t/h of water to recover all of the ethanol, i.e. much less than in the prior art examples.

2.5—First Butadiene Separation Step, Alternative 4

This example differs from the previous example in that the fraction of the ethanol effluent obtained from the step for treatment of the effluents was pre-cooled to 14° C. before being used to scrub the previously compressed vapour effluent from the butadiene conversion step. This scrub was used to recover all of the butadiene comprised in said vapour effluent.

The scrubbed gas effluent, free of acetaldehyde, was then scrubbed with recycled water in order to recover the ethanol. It was necessary to employ 0.4 t/h of water in order to recover all of the ethanol, i.e. more than 20 times less than in the prior art.

The reduction in the flow rate of water required for scrubbing meant that 13% of the flow rate of water at the inlet to the effluent treatment step could be reduced; as a consequence, this reduced the size of the separation equipment and its energy consumption.

2.6—Subsequent Butadiene Separation Step

The purified butadiene effluent obtained from the first butadiene purification step was supplied to a drying section by passing it in succession over an alumina, then over a zeolite 4A, in order to scrub all of the water which might have been present in said purified butadiene effluent. The effluent from the drying section formed the dry butadiene effluent. This dry butadiene effluent was then supplied to a cryogenic distillation column operated at an overhead pressure of 0.35 MPa, a bottom temperature of 34° C. and an overhead temperature of −33° C.

Finally, the distillation residue, known as the topped butadiene effluent, was supplied to a liquid-liquid extraction section using DMSO and cyclohexane.

A first scrubbing column was supplied overhead with 260 t/h of DMSO and at the bottom with 52 t/h of cyclohexane. This first column comprised 20 theoretical scrubbing stages. The bottom product from the first column was sent to a second scrubbing column comprising 10 theoretical stages.

The overhead product from this second scrubbing column was treated in a distillation column, which meant that the butadiene could be separated from the cyclohexane; it comprised 24 theoretical stages and operated with a reflux ratio of 8.

The overhead product from the first scrubbing column was treated in a distillation column in order to separate the butenes from cyclohexane; it comprised 26 theoretical stages and operated with a reflux ratio of 10.

99.3% of the butadiene entering the second butadiene separation step was recovered as a product with a purity of 99.88% by weight.

A purified butadiene effluent was obtained from the outlet from the liquid-liquid extraction section for which the butadiene content was 99.88% by weight. The butadiene losses over all of the purification steps (calculated from the ratio of the flow rate of pure butadiene included in the purified butadiene effluent over the flow of pure butadiene included in the effluent from the butadiene conversion reactor) was less than 0.8% by weight.

The arrangement of the steps and recycles of the invention, in particular by preventing the accumulation of impurities, meant that almost all of the compounds which had not reacted could be recycled. Thus, despite a low conversion per pass in the reactors, comparable with the prior art, the overall yield in $t_{butadiene\ produced}$ per $t_{converted\ ethanol}$ was 41%. Carrying out the recycles of the invention means that the overall yield can be improved by more than 20 points compared with a situation without recycling as well as recovery and upgrading of all of the acetaldehyde present in the effluent from the second conversion step. Thus, more than 99.9% of the ethanol included in the feed for the process is upgraded.

The invention claimed is:

1. A process for the production of butadiene from an ethanol feed comprising at least 80% by weight of ethanol, comprising at least:
    A) converting ethanol to acetaldehyde, in at least one reaction section supplied with at least a fraction of ethanol-rich effluent obtained from E1) to obtain a reaction effluent, wherein said at least one reaction section is operated at a pressure of 0.1 to 1.0 MPa and at a temperature of 200° C. to 500° C. in the presence of a catalyst, separating reaction effluent obtained from said at least one reaction section into at least one hydrogen effluent in gaseous form and at least one ethanol/acetaldehyde effluent in liquid form;
    B) converting an ethanol/acetaldehyde mixture into butadiene to obtain a conversion effluent, in at least one reaction section wherein said ethanol/acetaldehyde mixture is a combination of at least a fraction of said ethanol/acetaldehyde effluent obtained from A), with a liquid ethanol-rich effluent and with a fraction of acetaldehyde-rich effluent, wherein said ethanol/acetaldehyde mixture is suplied to said at least one reaction section, wherein said at least one reaction section is operated in the presence of a catalyst, at a temperature of 300° C. to 400° C., and at a pressure of 0.1 to 1.0 MPa, wherein flow rates of the supply combination to said at least one reaction section is regulated at an ethanol/acetaldehyde molar ratio of 1 to 5, separating in a separation section a conversion effluent from said at least one reaction section into at least one gaseous effluent and a liquid effluent;
    C1) hydrogen treatment, in at least one compression section compressing said at least one hydrogen effluent obtained from A) to a pressure of 0.1 to 1.0 MPa thereby producing a compressed hydrogen effluent, and in a gas-liquid scrubbing section supplied, at a temperature −30° C. to 15° C., with a fraction of ethanol rich effluent obtained from E1) and with a fraction of said ethanol/acetaldehyde effluent obtained from A), and supplied, at a temperature of 25° C. to 60° C., with said compressed hydrogen effluent, and producing at least one liquid ethanol-rich effluent and a purified hydrogen effluent from the gas-liquid scrubbing section; supplying the at least one liquid ethanol-rich effluent to the at least one reaction section in B);
    D1) extracting butadiene by compressing, in at least one compression section said at least one gaseous effluent obtained from B) to a pressure of 0.1 to 1.0 MPa, to obtain a compressed gaseous effluent that is then cooled to a temperature of 25° C. to 60° C. by scrubbing said compressed gaseous effluent in a gas-liquid scrubbing section comprising a scrubbing column supplied overhead, at a temperature of −20° C. to 20° C., with an ethanol stream comprising said ethanol feed for the process and/or a fraction of the ethanol-rich effluent obtained from E1) and at the bottom with said compressed gaseous effluent that is cooled to a temperature of 25° C. to 60° C. to produce an overhead effluent of gaseous by-products and a bottom liquid effluent from the gas-liquid scrubbing section, and by distilling in a distillation section operated at a pressure of 0.1 to 1 MPa, at least the liquid effluent obtained from B) and said bottom liquid effluent from said gas-liquid scrubbing section of D1), producing an unrefined butadiene effluent and an ethanol/acetaldehyde/water effluent from the distillation section;

D2) a first butadiene purification in at least one gas-liquid scrubbing section supplied at bottom with the unrefined butadiene effluent obtained from D1) and supplied at head with a stream of water which is a stream of water with an origin external to said process for the production of butadiene and/or a fraction of water-rich effluent obtained from E1), said at least one gas-liquid scrubbing section producing a pre-purified butadiene effluent from the head and a spent water effluent from the bottom;

D3) subsequently purifying butadiene, from said pre-purified butadiene effluent obtained from D2), to produce at least one purified butadiene effluent;

E1) treating at least the water/ethanol/acetaldehyde raffinate obtained from E2), and producing at least one ethanol-rich effluent, an acetaldehyde-rich effluent and a water-rich effluent wherein at least a fraction of the at least one ethanol-rich effluent is supplied to the at least one reaction section in A), wherein at least a fraction of the at least one ethanol-rich effluent is supplied to the gas-liquid scrubbing section in C1), wherein a fraction of the at least one ethanol-rich effluent is comprised in ethanol stream in D1), wherein at least a fraction of said acetaldehyde rich effluent is supplied to the at least one reaction section in B), and wherein a fraction of said water rich effluent is the stream of water that supplies to the head of the at least one gas-liquid scrubbing section in D2);

E2) eliminating impurities and brown oils from at least the ethanol/acetaldehyde/water effluent obtained from D1), and from the water-rich effluent obtained from E1), and producing at least one water/ethanol/acetaldehyde raffinate, a light brown oil effluent and a heavy brown oil effluent; and F) scrubbing with and a fraction of the water-rich effluent obtained from E1) the at least one effluent of gaseous by-products obtained from D1), and producing at least one alcohol-containing water effluent.

2. The process according to claim 1, in which a final hydrogen treatment C2) is carried out at the end of C1), C2) comprising at least one gas-liquid scrubbing section supplied with the purified hydrogen effluent obtained from C1) and with a pure water effluent originating from outside the process or with the water-rich effluent obtained from E1), and producing a purified hydrogen effluent and a spent water effluent.

3. The process according to claim 1, in which the pre-purified butadiene effluent obtained from D2) undergoes a second butadiene purification D2bis) before being supplied to the subsequent butadiene purification D3), D2bis) comprising at least one scrubbing section having a bottom and a head, supplied at the bottom with said pre-purified butadiene effluent obtained from D2), supplied at the head with an absorbent solution.

4. The process according to claim 3, in which said absorbent solution is an aqueous solution with a pH of more than 10, adjusted by adding sodium or potassium hydroxide.

5. The process according to claim 3, in which said absorbent solution is an aqueous sodium or potassium bisulfite solution having a pH of range 5 to 8.

6. The process according to claim 3, in which said absorbent solution is an aqueous solution containing a hydrazine compound.

7. The process according to claim 1, in which E2) comprises at least one scrubbing/back-scrubbing section, a section distillating light brown oils, and a section distillating of heavy brown oils, said scrubbing/back-scrubbing section being supplied at an intermediate point with said ethanol/acetaldehyde/water effluent obtained from D1), at bottom with a hydrocarbon effluent and overhead with a fraction of the water-rich effluent obtained from E1), wherein said at least one scrubbing/back-scrubbing section produces a hydrocarbon scrub extract overhead and said at least one water/ethanol/acetaldehyde raffinate at bottom; said section distilling light brown oils being supplied with said hydrocarbon scrub extract, and producing, as a distillate, said light brown oil effluent and a hydrocarbon residue, said section distilling heavy brown oils being supplied with a fraction of said hydrocarbon residue representing from 5% to 30% by weight of the total flow rate of said hydrocarbon residue and producing a hydrocarbon distillate and, as a residue, said heavy brown oil effluent, said hydrocarbon distillate and remaining fraction of said hydrocarbon residue being mixed in order to constitute the hydrocarbon effluent supplying the bottom of said at least one scrubbing/back-scrubbing section.

8. The process according to claim 1, in which A) is also supplied with at least a fraction of said ethanol feed.

9. The process according to claim 1, in which said at least one reaction section B) is also supplied with the at least one ethanol-rich effluent obtained from E1).

10. The process according to claim 1, in which said at least reaction section B) is also supplied with an external acetaldehyde stream.

11. The process according to claim 1, in which C1) is not supplied with any other stream.

12. The process according to claim 1, in which the at least one ethanol-rich effluent obtained from E1) is supplied to said gas-liquid scrubbing section in C1) at a temperature which is below that of said at least one ethanol/acetaldehyde effluent obtained from A).

13. The process according to claim 1, in which D3) comprises at least one drying cryogenic distillation and butadiene/butenes separation by liquid-liquid extraction.

14. The process according to claim 1, in which D3) comprises at least one distillation and an extractive distillation.

15. The process according to claim 1, in which the treating in E1) is also supplied with a fraction of said ethanol feed.

* * * * *